United States Patent
Shifrin et al.

(10) Patent No.: US 7,651,498 B2
(45) Date of Patent: Jan. 26, 2010

(54) STERNAL CLOSURE SYSTEM, METHOD AND APPARATUS THEREFOR

(75) Inventors: Edward G. Shifrin, 64 Ha-Shahar Street, Raanana 43565 (IL); Gennady S. Nickelshpur, Haifa (IL); Mordehy D. Shvartsman, Haifa (IL); Mark A. Umansky, Haifa (IL)

(73) Assignee: Edward G. Shifrin (IL)

( * ) Notice: Subject to any disclaimer, the term of this patent is extended or adjusted under 35 U.S.C. 154(b) by 0 days.

(21) Appl. No.: 10/561,354

(22) PCT Filed: Feb. 19, 2004

(86) PCT No.: PCT/IL2004/000155

§ 371 (c)(1),
(2), (4) Date: Dec. 19, 2005

(87) PCT Pub. No.: WO2004/078218

PCT Pub. Date: Sep. 16, 2004

(65) Prior Publication Data

US 2006/0161161 A1    Jul. 20, 2006

(30) Foreign Application Priority Data

Mar. 9, 2003    (IL) .................................... 154814

(51) Int. Cl.
*A61B 17/064*    (2006.01)
*A61B 17/58*    (2006.01)

(52) U.S. Cl. .......................................... 606/75; 606/104

(58) Field of Classification Search .................. 606/75, 606/104
See application file for complete search history.

(56) References Cited

U.S. PATENT DOCUMENTS

| | | | |
|---|---|---|---|
| 3,832,139 A * | 8/1974 | Runck et al. ................. | 422/100 |
| 3,875,648 A * | 4/1975 | Bone ............................ | 29/417 |
| 4,434,796 A * | 3/1984 | Karapetian et al. ............ | 606/75 |
| 4,676,245 A | 6/1987 | Fukuda | |
| 4,841,960 A | 6/1989 | Garner | |
| 5,520,700 A * | 5/1996 | Beyar et al. .................. | 606/139 |
| 5,735,183 A * | 4/1998 | Sasaki et al. .................. | 81/473 |
| 6,051,007 A | 4/2000 | Hogendijk | |
| 6,056,751 A * | 5/2000 | Fenton, Jr. .................... | 606/72 |
| 6,368,342 B1 | 4/2002 | Lemer | |
| 6,497,707 B1 | 12/2002 | Bowman et al. | |
| 6,554,852 B1 * | 4/2003 | Oberlander .................. | 606/232 |

* cited by examiner

*Primary Examiner*—Eduardo C Robert
*Assistant Examiner*—Ellen C Hammond
(74) *Attorney, Agent, or Firm*—Ostrolenk Faber LLP

(57) ABSTRACT

There is provided a sternal closure system for re-approximating the left and right halves of a patient's longitudinally incised sternum during a surgical procedure in the thoracic cavity. The system includes a first anchor, disposed inside the left half of the sternum, a second anchor, disposed inside the right half of the sternum, and a fixing element for rigid connection between the first and the second anchors, respectively disposed within the left and right halves of the sternum, facilitating separation of the left and right halves of the sternum closed in this way, in case of post-operative emergency surgical procedures. An apparatus for fixing and removing the anchors is also provided.

35 Claims, 21 Drawing Sheets

View A

View B

C – C

D – D

View E

STERNAL CLOSURE SYSTEM, METHOD AND APPARATUS THEREFOR

FIELD OF THE INVENTION

The present invention relates generally to surgical devices, and more particularly to devices and methods for reapproximating the sternal halves of a patient's severed or separated sternum following a partial or medial sternotomy.

BACKGROUND OF THE INVENTION

Various types of surgical procedures are currently performed to investigate, diagnose, and treat diseases involving a tissue or organs located in a patient's thoracic cavity (e.g., the heart, lungs, and the like).

Using current techniques, many of those procedures typically require a partial or median sternotomy to gain access into the patient's thoracic cavity. A partial or median sternotomy is a procedure by which a saw or other appropriate cutting instrument is used to make a midline, longitudinal incision along a portion or the entire axial length of the patient's sternum, allowing two opposing sternal halves to be separated laterally. A large opening into the thoracic cavity is thus created, through which a surgeon may directly visualize and operate upon the heart and other thoracic organs or tissues.

Following the surgical procedure within the thoracic cavity, the two severed or separated sternal halves must be reapproximated (closed). Traditionally, the sternal halves have been reapproximated with stainless steel wires which are wrapped around or through the sternal halves so as to exert medial compression thereon and twisted together to approximate the sternum. There are inventions disclosed and claimed in Pasque, Michael U.S. Pat. No. 5,423,821 and WO9641581A1, Monassevith, Leonid U.S. Pat. No. 6,171,320 and IL 119911.

Pasque discloses a device and method for closing the sternum using selected plastics or nylon fibers or other strand expandable materials for suturing. A fastener device is also disclosed.

Monassevitch discloses a surgical clip including three lengths of wire integrally formed of a shape memory alloy, two of which form closed geometrical shapes similar in configuration and magnitude to each other, and third connects the first two.

Other methods of sternum repair include the use of band or strap assemblies. Among them are inventions disclosed and claimed in Green, David et al., U.S. Pat. No. 5,417,698 and EP 592960A2; Burgess, Frank et al., U.S. Pat. No. 4,944,753; Golds, Ellen et al., U.S. Pat. Nos. 5,356,412; 5,356,417; EP 596277A1 and EP 597258A1; Sutherland, Lloyd et al., U.S. Pat. No. 4,730,615; Johnson, Greg et al., U.S. Pat. Nos. 6,045,572; 6,080,185; PCT/US99/24164 and Barry, Joseph U.S. Pat. No. 4,583,541.

Such assemblies typically include a locking mechanism, which secures a band or strap in a closed looped configuration about the sternum positions.

For example, Green, David et al., U.S. Pat. No. 5,417,698 and EP 592960A2 disclose an instrument for tightening wound closure elements around human sternum. The instrument includes two handles pivotally attached to one another and movable between an open and closed position. A retaining system is also provided to tighten wound closure material.

Burgess, Frank et al. in U.S. Pat. No. 4,944,753 disclose a method and device for producing an artificial retro-sternal tunnel or space at the conclusion of a sternotomy, and an implantable elongate member for closure of the longitudinally severed sternum.

Golds, Ellen et al. in U.S. Pat. Nos. 5,356,412; 5,356,417; EP 596277A1 and EP 597258A1 disclose a strap assembly to be looped about split portions of sternum including a flexible elongated member and a buckle member with a clamp element rotatably mounted within buckle member from a non-strap securing position to the strap securing position in response to tensional forces exerted on the strap during tensioning thereof about the tissue portion.

Sutherland, Lloyd et al. in U.S. Pat. No. 4,730,615 disclose a sternum closure device made of biocompatible metal coated with a biocompatible polymer and comprising a head portion, tail portion and flexible spine portion. The head portion includes a locking tang to prevent backward movement of the spine portion once it is received and engaged in the head portion.

Johnson, Greg et al. in U.S. Pat. Nos. 6,045,572; 6,080,185 and PCT/US99/24164 disclose a system for closing together two sides of sternum, including a first and second grommets adapted to be disposed on two sides of the sternum, a wire suture, a mechanism for placing a grommet into the sternum and a placement tool. Besides, they disclose a method of threading a wire suture through a hole in a sternum and a method of bringing together two sides of a sternum.

Finally, Barry, Joseph in U.S. Pat. No. 4,583,541 discloses a sternum closure device having an elongated strap-like member provided with a flat back surface which flatly overlies the anterior surface of a severed or separated sternum. The forward surface of the member is convex and longitudinally grooved for nesting the tied or twisted end portions of suture wires extending across the posterior of the sternum and projecting forwardly through cooperating pairs of holes formed in the member on opposing sides of the groove.

While utilization of steel wires and strap assemblies have been widely accepted for sternum repair, these devices present a number of disadvantages. Steel wires can and do break, and provide insufficient (non-uniform) clamping force resulting in sternal nonunion. Steel wires are difficult to maneuver and place around the sternum. The cut ends of the steel wires are also sharp and can pierce through the surgeon's gloves or fingers. In addition, the small diameter of the steel wires can cause the wires to migrate into or through the tissue surrounding the sternum region or into the sternal bone itself over time. This can lead to significant patient pain and discomfort in addition to slowing the postoperative recovery and increasing the risk of sternal infection. Moreover, the strap mechanisms of band assemblies are often relatively structurally complex and are difficult to precisely apply about the sternum. There are also healing problems associated with the use of steel wires and band assemblies due to improper forces exerted by these devices which can cause unwanted bone movements leading to raking and rubbing of surrounding tissue or bone.

Several other techniques of sternal reapproximation have been proposed both for primary closure following a median sternotomy and for reclosure following post-operative emergency surgical procedures. One such sternal closure technique and kit for performing same is described in Zurbrugg, Heinz, U.S. Pat. No. 6,030,410. According to this method, staples are applied to the sternal halves to reinforce the bone adjacent to the suture outlets so as to prevent the suture from cutting into the bone. As each suture loop is tightened to adapt the sternum, the suture loop abuts the staples adjacent the suture outlets. A sterile surgical staple gun is employed to install the staples in the sternal halves.

This method and device and other similar to them, are not optimal, however, because they require direct fixation of the wire to the bone with staples. This makes difficult reentry into the thoracic cavity.

Gabbay, Slomo in U.S. Pat. No. 4,792,248 describes a sternum closure device used for holding together the halves of a split sternum. The device described therein is composed of two plates, one anterior and one posterior to the sternum, that are fixed to each other and to the sternum by means of threaded rods into internally threaded posts positioned in predrilled holes through the bone on either side of the sternotomy.

There are also known methods and apparatus for stapling together severed sternum, including a staple applying tool adapted to drive the staples into or around the sternum halves and lock together these sternum halves. Among them there are U.S. Pat. No. 5,163,598 by Peters, Rudolf et al. and U.S. Pat. No. 4,122,989 by Kapitanov, Nikolai et al. As disclose Peters, Rudolf et al., the sternum stapling apparatus includes a distal shoe with staple forming anvil, a piston within caliper assembly, a staple cartridge and the adjusting tool including a pair of jaws, one having a fulcrum lug and the other having two spaced lugs, whereby the staple may be bent by closure of the lugs together to decrease the linear spacing of the staple legs and increase the abutting force of the bone tissue portions. Kapitanov, Nikolai et al. disclose a surgical instrument for suturing sternal fragments with metal staples including an anvil unit which has two elongated jaws aligned with each other and having inner surfaces facing each other and formed with longitudinal guiding grooves for a staple. The front ends of the jaws carry anvils for bending the tips of the staples. In similar apparatus there may be used special compression bone clips and staples such as described by Wevers, Henk et al. in U.S. Pat. No. 4,444,181 and Murray, William in U.S. Pat. No. 3,960,147.

This device, and others similar to it, are not optimal, however, because they make reentry into the thoracic cavity through the sternotomy extremely difficult if a medical emergency arises during the surgical procedure or post-operative requiring relatively quick access to the organs and/or tissues within the patient's thoracic cavity.

THE PRIOR ART

To overcome the problems inherent in direct fixation devices, another technique of sternal reapproximation has been proposed which employs overlapping sternal plates which can be removably joined to one another. In Levin, Scott in U.S. Pat. No. 6,007,538; Hogendijk, Mike et al., in U.S. Pat. No. 6,051,007 a separable sternal clamping device is disclosed which includes generally J or C-shaped sternal engagement legs. The sternal clamp plates are laterally adjustable relative to one another but can be rigidly joined by, for example, a set of machine screws (see Levin, Scott, U.S. Pat. No. 6,007,538) or by lock mechanism (see Hogendijk, Mike et al., in U.S. Pat. No. 6,051,007). The threaded coupling of the machine screw or lock coupling of the locking mechanism with the sternal plates removably secures these plates one to another in overlapping relationship without lateral shifting occurring over time, allowing easy reopening of the sternum if necessary.

Other improvements to sternal clamping devices and methods for sternal reapproximation are needed which are easily assembled, and which provide a staple and uniform clamping force and a well-approximated closure that allows bone healing to occur. The devices and methods should facilitate reopening of the sternum if necessary, e.g., in case of a medical emergency requiring the surgeon to have access to the patient's thoracic cavity. Preferably, the devices should be made from a biocompatible, radioreflectible material which facilitates post-operative radioscopic viewing of the sternum and thoracic cavity condition. The lateral dimension between the clamp members of the devices should also be adjustable to fit a particular patient's sternum. New surgical tools are also required to assist the surgeon in properly positioning the clamping devices during the reapproximation procedure and easily removing them if necessary.

An object of the present invention is to provide a reliable closure of a patient's sternum on completion of sternotomy, by placing fixing means evenly along the sternum incision line, irrespective of its (sternum) configuration.

Another object of the invention is to provide easy placement and, if necessary, removal of these fixing means, as well as efficacy and convenience of surgeon' work.

SUMMARY OF THE INVENTION

The present invention provides improved devices and method for reapproximating the sternal halves of a patient's sternum following a median or partial sternotomy that facilitates ready access to the thoracic cavity during or after a medical procedure (e.g., in the case of a medical emergency) and which overcomes sternal nonunion problems inherent in previous sternal closure devices.

The subject-matters of the present invention are a system and method for securing to one another the left and right half of a patient's incised sternum during a surgical procedure in the thoracic cavity.

This system comprises a first, at least one anchor means, adapted to be disposed within the left half of sternum, a second, at least one anchor means adapted to be disposed within the right half of sternum, as well as at least one fixing means adapted for rigid connection to one another of these first and second anchor means. Besides, the system comprises an apparatus for simultaneously placing in the sternum both the first, at least one anchor means, adapted to be disposed within the left half of sternum, and the second, at least one anchor means adapted to be disposed within the right half of sternum. The system also comprises a fixing apparatus for placing the fixing means, as well as an apparatus for removing this fixing means. Thereby there is performed a rigid connection to one another of the left half and right half of patient's incised sternum during a surgical procedure within the thoracic cavity, as well as separation of the left and right halves of sternum closed in this way, in case of urgent operations.

According to a first aspect of the invention, the first, at least one anchor means, adapted to be disposed within the left half of sternum, and the second, at least one anchor means, adapted to be disposed within the right half of sternum, are machine screws having an external thread of one direction. These anchor means may be as well machine screws having external thread of different directions.

According to a second aspect of the invention, the anchor means have heads provided with means for grasping and rotating them by an apparatus for simultaneous placing of these anchor means. The grasping means are generally shaped as grooves on the heads side surface, and rotating means are generally cross slots or hexahedral holes on the heads end surface.

According to a third aspect of the invention, there is proposed at least one fixing means adapted for rigid securing to one another the respective first and second anchor means. It is substantially shaped as a staple having a body and at least two legs extending from this body in a substantially perpendicular relationship. The staple body may be also curved, and its legs slightly curved. Owing to these legs the staple is adapted for rigidly securing to one another the first and second anchor means. To this effect, both the first, and second anchor means, each have an internal axial passage adapted for disposing therein, substantially tightly, one of the respective staple legs.

According to a next aspect of the invention, the anchor means and staples made of FDA approved materials, mainly of metals and alloy group, consist of stainless steel, titanium, tantalum as well as titanium or tantalum alloys. The anchor means and staples also may be made of FDA approved biodegradable material.

Each embodiment of the apparatus for simultaneous placing in the sternum the first and second anchor means comprises a power means to generate a torque, a means for transmitting torque simultaneously to the first and second anchor means, means for searching and grasping simultaneously the first and second anchor means, as well as a means for retaining and simultaneous bringing these anchor means to this means for their searching and grasping.

The power means for generating a torque comprises one of the means of a group including an electric, pneumatic or hydraulic engine.

The means for transmitting torque simultaneously to the first and second anchor means is generally a gear box having one drive shaft and at least two driven shafts. On the driven shafts there are mounted spring-loaded heads forming the means for searching and grasping simultaneously the first and second anchor means.

Further, the first embodiment of the apparatus for simultaneously placing in the sternum the first and second anchor means comprises a frame means with vertical guides, and the means for retaining and simultaneously bringing of the first and second anchor means to the means for their searching and grasping comprising a spring-loaded cartridge disposed within this frame means for stepping horizontal movement towards this means for searching and grasping. In the described apparatus the power means for generating torque, means for transmitting torque simultaneously to the first and second anchor means, as well as the means for searching and grasping simultaneously the first and second anchor means, are formed as a single unit disposed on vertical guides of the frame means reciprociprocably relative to the latter.

According to the second embodiment of the apparatus for simultaneously placing in the sternum the first and the second anchor means, this apparatus comprises a frame means with two horizontal plates disposed in parallel relationship, and at least one vertical guide rigidly connected with at least one of these plates. The means for retaining and simultaneously bringing the first and second anchor means to the means for their searching and grasping contains two spring-loaded rotary drums disposed between the plates within the frame means and capable of performing stepping synchronous swinging about their vertical axes in direction to the means for searching and grasping these anchor means. In this embodiment, as in the previous one, the power means for generating torque, means for transmitting the torque simultaneously to said first and second anchor means and means for searching and grasping simultaneously the first and second anchor means are formed as a single unit disposed on at least one vertical guide of the frame means reciprocably relative to the latter.

The first embodiment of the claimed fixing apparatus for placing the fixing means adapted for rigidly securing to one another the respective first and respective second ancor means comprises at least two levers, first and second, each of them having a proximal end and distal end. These levers are pivotally connected to one another, spring-loaded relative to one another and provided with handles at their distal ends and means for grasping the heads of anchor means at their proximal ends. The fixing apparatus also has at least one spring-loaded third lever pivotally connected to the first lever or to the second lever and provided with a handle at its distal end. At its proximal end the third lever is provided with a means for bringing the fixing means simultaneously inside these first and second anchor means, which is shaped substantially as a pusher. Besides, the fixing apparatus has a means for retaining and by the piece delivery of fixing means, comprising generally a movable spring-loaded die with grooves for disposing fixing means.

The means for grasping the heads of anchor means comprise two protrusions facing one another, one of which is disposed at the proximal end of the first lever, and the second at the proximal end of the second lever, and these protrusions have at their free ends recesses, matching in shape the grooves on the side surface of heads of respective anchor means.

The means for retaining and by the piece delivery of fixing means in the fixing apparatus, comprising a movable spring-loaded die with grooves for disposing these fixing means, is mounted in a guide to perform stepping linear movement. This guide is movably connected to the first lever or the second lever of this fixing apparatus.

According to the second embodiment, the fixing apparatus for placing the fixing means contains at least two levers, the first and the second, each of them having a proximal end, a distal end, these levers being pivotally connected together and provided with handles at their distal ends, with means for mutual fixing of handles when brought together, as well as with means for grasping the heads of anchoring means at their proximal ends. The apparatus also contains at least one third lever pivotally connected with a bearing plate rigidly secured on the first lever or second lever. This third lever is provided with a handle at its free end, and by its middle pivotally connected with the means for bringing the fixing means inside the first and second anchor means shaped substantially as a pusher. Besides, the apparatus contains a means for retaining and by the piece delivery of fixing means formed substantially as a cartridge enclosing spring-loaded fixing means disposed right up to one another.

In this embodiment the apparatus also has means for grasping the heads of anchor means formed as protrusions facing one another, one of which is disposed at the proximal end of the first lever, and the second at the proximal end of the second lever. These protrusions have at their free ends recesses matching in shape the grooves on the side surface of heads of respective anchor means.

In the second embodiment the fixing apparatus contains at least one third lever, means for retaining and by the piece delivery of fixing means formed substantially as a cartridge, as well as a means for bringing the fixing means inside the first and second anchor means formed substantially as a pusher, all these being formed as a single unit. This single unit is pivotally connected with a bearing plate rigidly secured on the first lever or second lever and is capable of folding back in vertical plane to provide visualization of means for grasping anchor means or returning to operative position with simultaneously rigidly fixing the cartridge at proximal ends of the first and second levers of the fixing apparatus.

And at last, the system comprises an apparatus for removing the fixing means whenever a post-operative surgical procedure is necessary within the thoracic cavity. It contains a hollow body having a handle extending therefrom, and in its lower part—a bifurcated stop. There is also a spring-loaded grasping member movably disposed within this body and a pressure lever pivotally mounted within the upper part of this hollow body. This pressure lever has a handle extending substantially in the same direction as the handle of said hollow body, and a free end located within the hollow body and operatively connected with the spring-loaded grasping member.

The last aspect of the claimed invention is a method for reapproximatimg the patient's left and right sternal halves after a surgical procedure in the thoracic cavity. This method includes several successive steps.

First, penetrating, before incising the sternum into left and right halves, at least one pair of anchor means in such a manner, that one of them is placed in the future left half of sternum, and the second in the future right half of sternum. In this case one of anchor means in this pair is a respective first, at least one, anchor means adapted to be disposed within the left half of sternum, and the second of anchor means in this pair is a respective second, at least one anchor means adapted to be disposed within the right half of sternum.

Then the placing of pairs of anchor means is repeated as many times as it is necessary to provide, on completion of a surgical procedure, a secure connection of the left and right halves of sternum.

Further, the sternum is incised, by a surgical procedure, into left and right halves, and the surgical operation is performed.

On completion of the surgical operation within the thoracic cavity, the left and right halves of sternum are reapproximated by using conventional techniques. Thereupon, the first and second anchor means are grasped by their heads by means of a fixing apparatus, bringing them towards one another, and thereby reapproximating, at a neseccary distance, the left and right halves of the incised sternum. Then the fixing means is placed and fixed tightly to secure the heads of first and second anchor means and creating thereby a rigid connection of the left and right halves of the incised sternum. The final procedure of placing the fixing means is repeated as many times as there are respective pairs of anchor means.

The above is a brief description of some deficiencies in the prior art and advantages of the present invention. Other features, advantages, and embodiments of the invention will be apparent to those skilled in the art from the following description, accompanying drawings and claims.

BRIEF DESCRIPTION OF THE DRAWINGS

The invention will now be described in conjunction with the following drawings in which like reference numerals designate like elements and wherein:

FIG. 4, 5 are the general view and side view of the first embodiment of an apparatus for simultaneous placing of pairs of anchor means;

FIG. 6 is a diagram of the proposed means for searching and grasping simultaneously two anchor means;

FIG. 7 is the A view of the proposed means for searching and grasping simultaneously two anchor means;

FIG. 8-11 are, in succession, the cartridge means for retaining and simultaneous pairwise delivery of anchor means to the means for their searching and grasping, as well as the B view of this cartridge means and its sections C-C and D-D;

FIG. 12 is an end view of an anchor means head;

FIG. 13, 14 are the side view and cross section view of the second embodiment of an apparatus for simultaneous placing of pairs of anchor means;

FIG. 15, 16 are the top view and longitudinal section of the rotary drum;

FIG. 17 is the longitudinal section along the axis of the rotary drum;

FIG. 18 is the general view of the proposed means for seraching and grasping anchor means;

FIG. 19, 20 is a general and a side view of the fixing apparatus;

DETAILED DESCRIPTION OF THE INVENTION

The invention is illustrated by drawings which show in detail two of the embodiments of the proposed system for securing to one another the left and right halves of a patient's incised sternum, as well as the method for applying this system.

Figure 1:
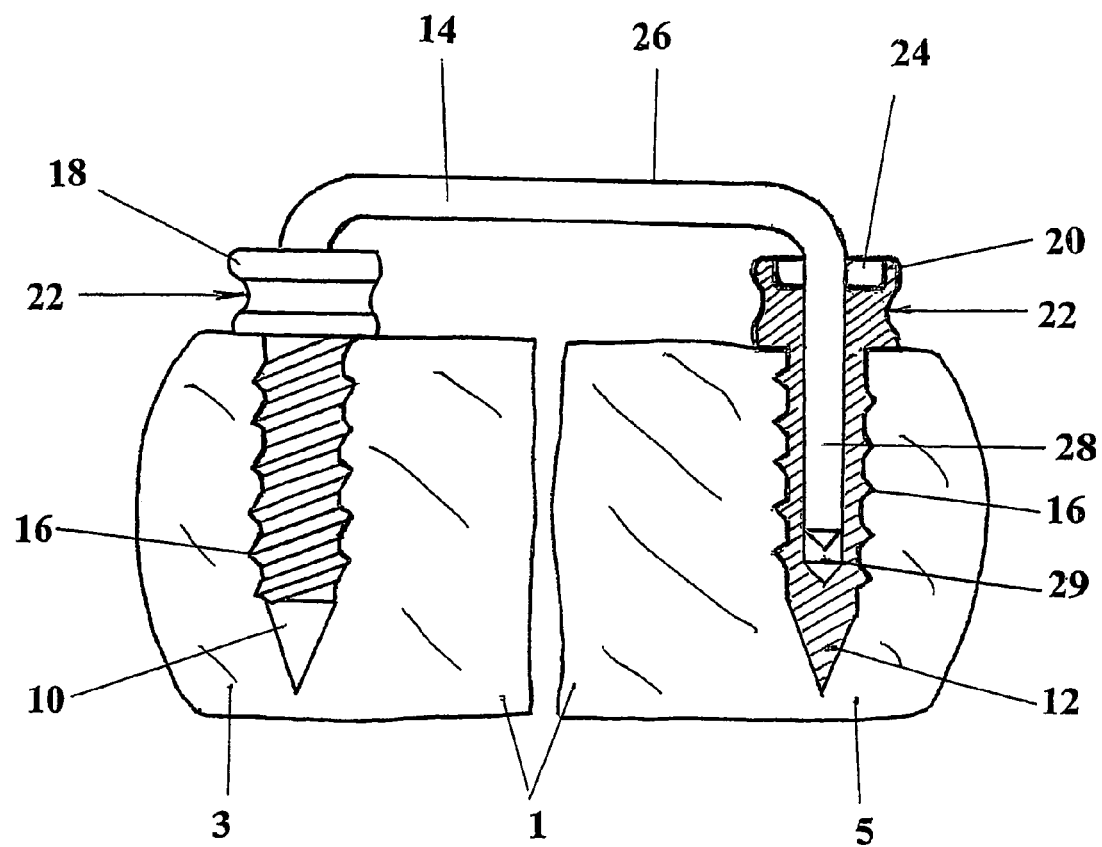
FIG. 1 is a perspective view of a sternal closure device consisting of two anchor devices and one fixing means.
Figure 12:
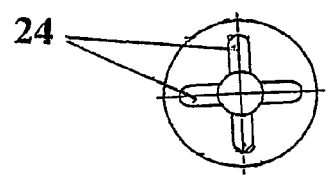

This system (FIG. 1) comprises, first of all, elements for closing sternum 1 incised into left 3 and right 5 halves. Among these elements there is an anchor means 10 adapted to be disposed within left half 3 of sternum 1, anchor means 12 adapted to be disposed within right half 5 of sternum 1, as well as fixing means 14 adapted for rigidly securing to one another these first 10 and second 12 anchor means. Anchor means 10 and 12 (FIG. 1) are formed as machine screws having an external thread 16 of one direction. These anchor means 10 and 12 may be also formed as machine screws having an external thread of different direction. Anchor means—machine screws 10 and 12 have heads 18 and 20 provided with means for their grasping and rotating. The means for grasping and rotating are generally shaped as grooves 22 on the side surface of heads 18 and 20 (FIG. 1), while means for rotating are generally shaped as cross-shaped slots 24 or hexahedral holes 24' on the end surface of heads 18 and 20 (FIGS. 1 and 12).

Figure 15:
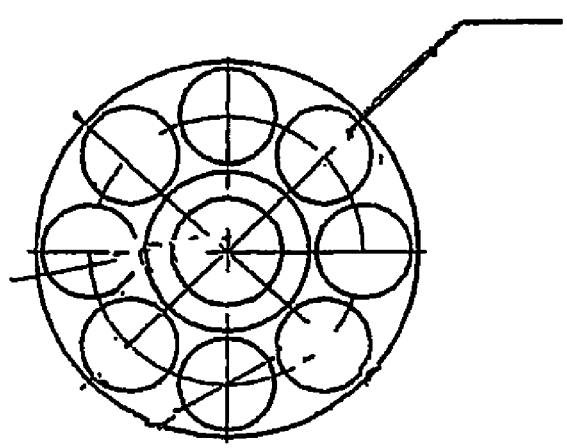
Figure 16:
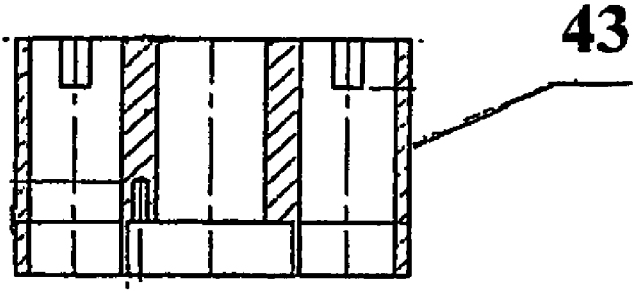
Figure 17:
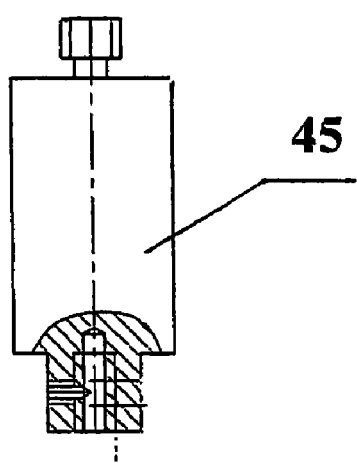
Figure 18:
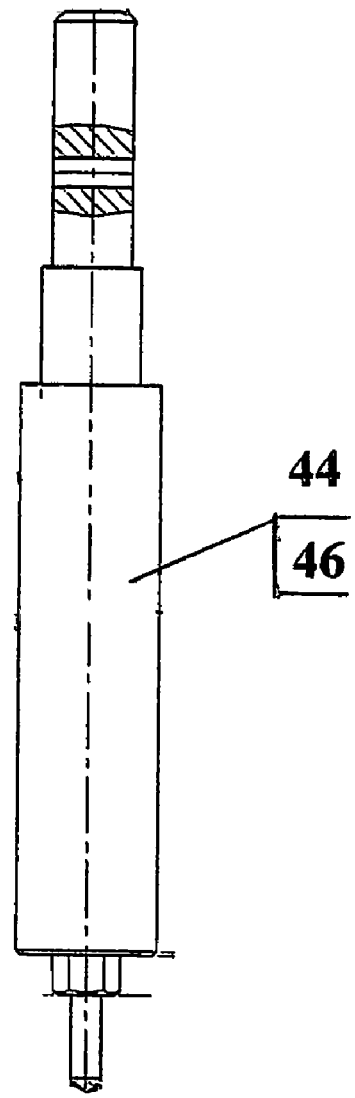
Figure 19:
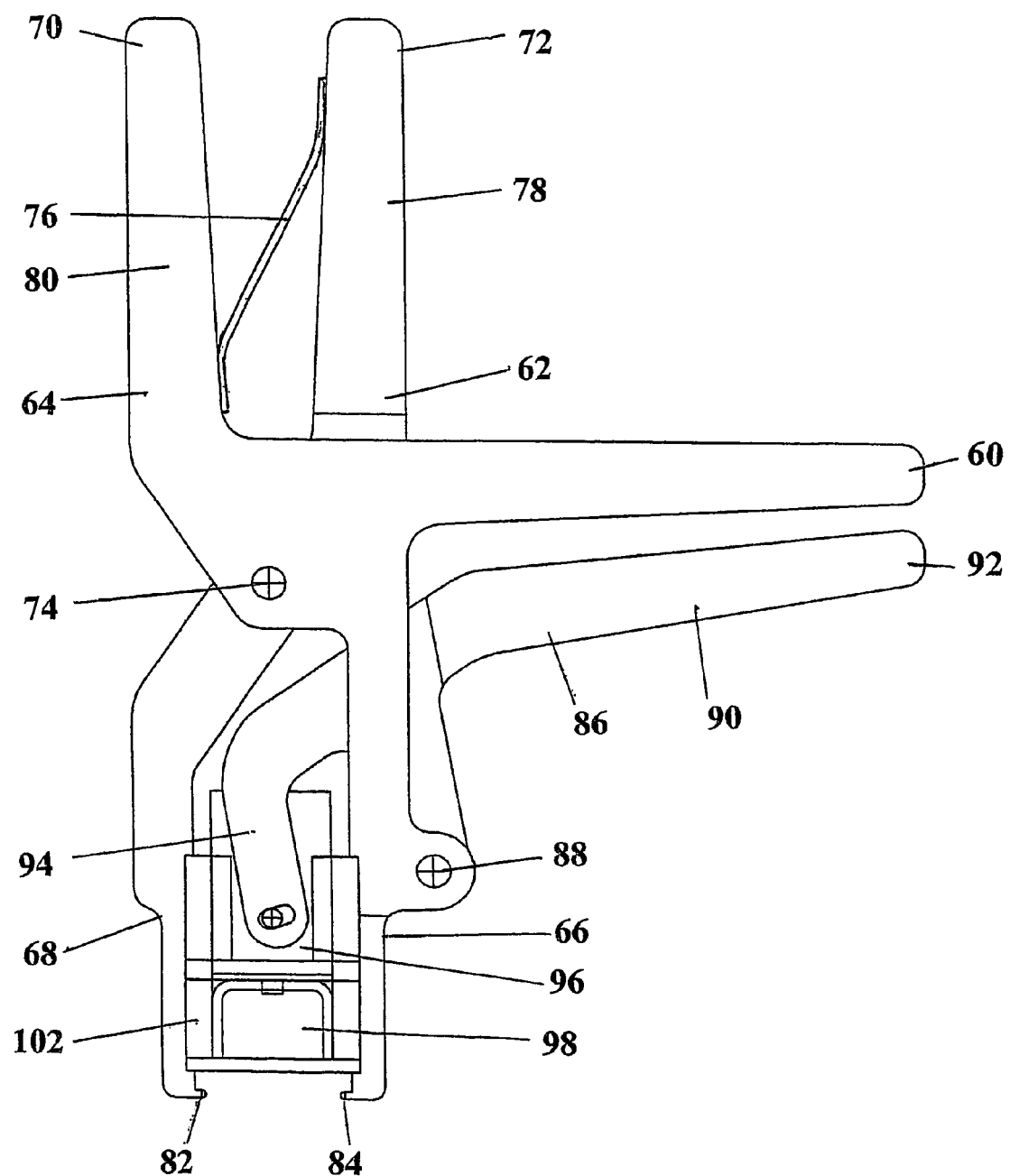
FIG. 19, 24 are the views of first embodiment of the proposed fixing apparatus, more concrete.
Figure 20:
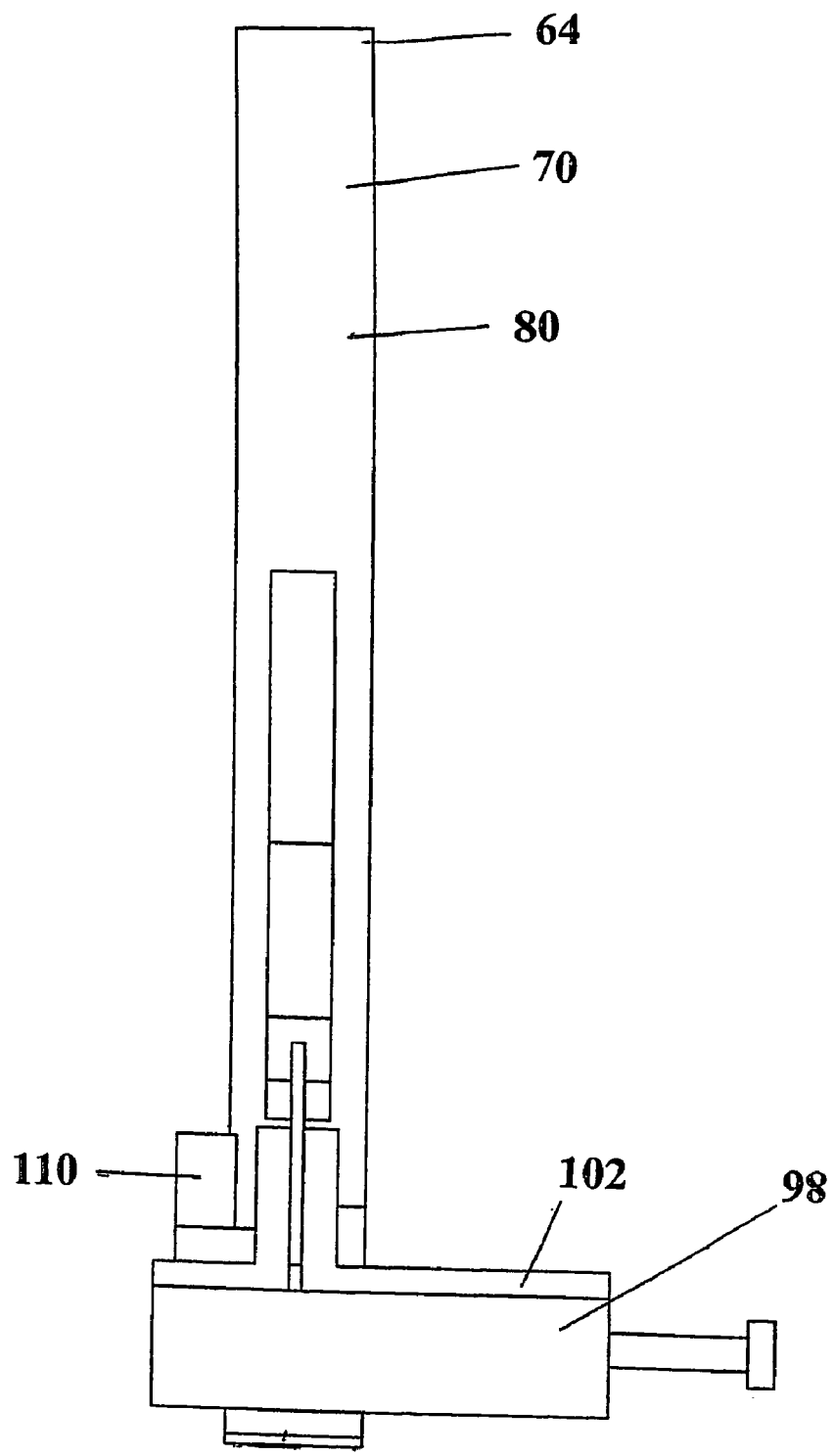
Figure 21:
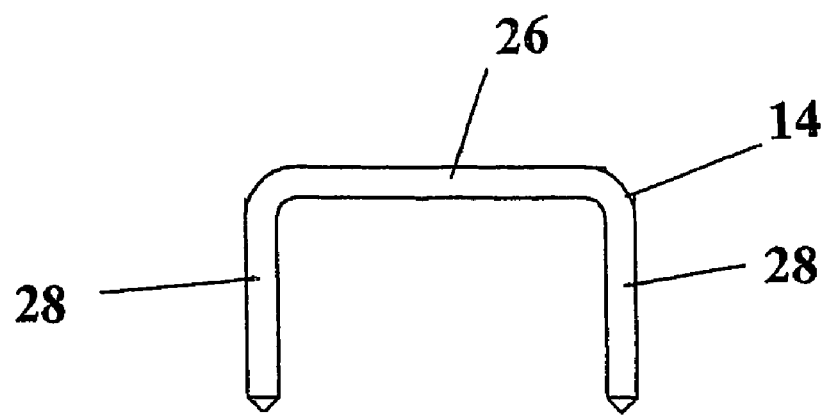
FIG. 21 is the proposed clamp for rigid fixation of anchor means.
Figure 22:
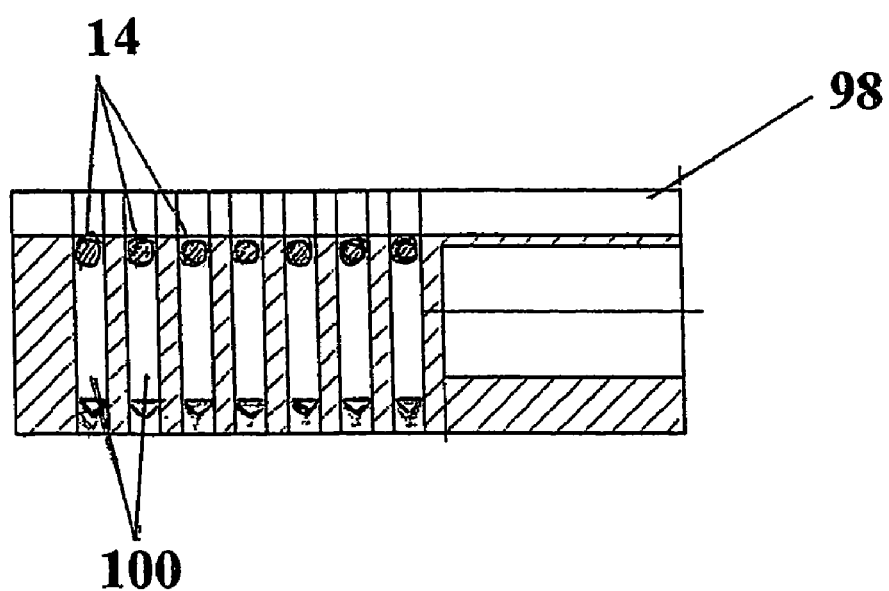
FIG. 22 is a longitudinal section of the movable die for retaining and by the piece delivery of staples.
Figure 23:
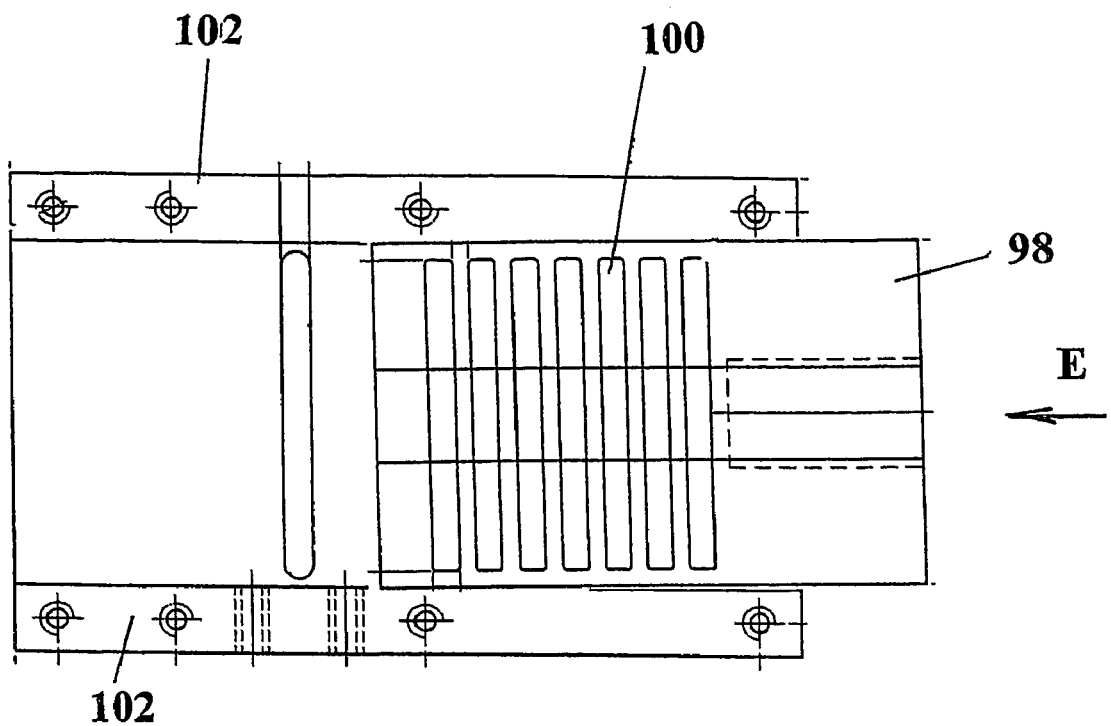
FIG. 23, 24 is the movable die for retaining and by the piece delivery of staples mounted inside the guide and their general view E.
Figure 24:
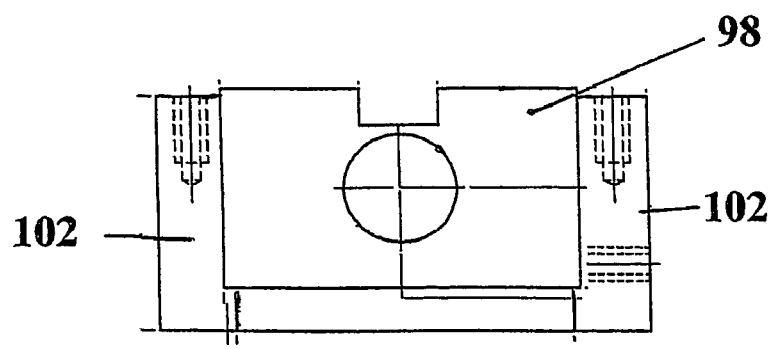

Fixing means 14 serving for rigid securing respective first and second anchor means 10 and 12 to one another is generally a staple (FIGS. 1 and 15) having a body 26 and at least two legs 28 extending from body 26 substantially in a perpendicular relationship. The staple body 26 may be curved in such a way that its middle approximates the surface of the left 3 and right 5 sternum halves (FIG. 27), while two legs 28 of fixing means 14 are slightly curved. Owing to legs 28 the fixing means—staple 14 is adapted to rigidly secure to one another screws 10 and 12. To this effect both screws 10 and 12 have an inner axial passage 29 adapted for disposing therein, preferably tightly, one of respective legs of the staple 14.

Figure 2:
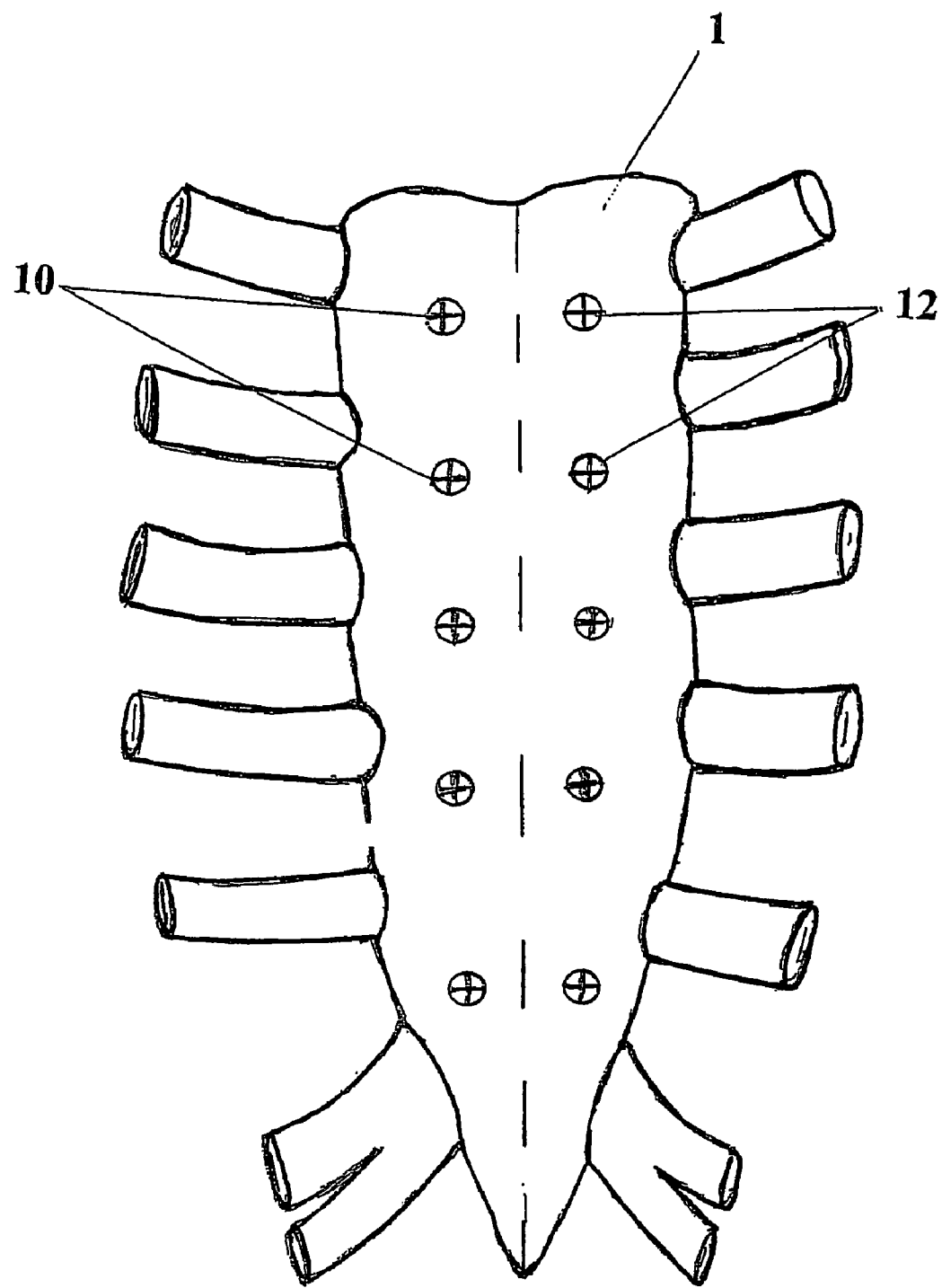
FIG. 2 is a diagram of placing anchor means inside the sternum before incising it into the left and right halves.
Figure 3:
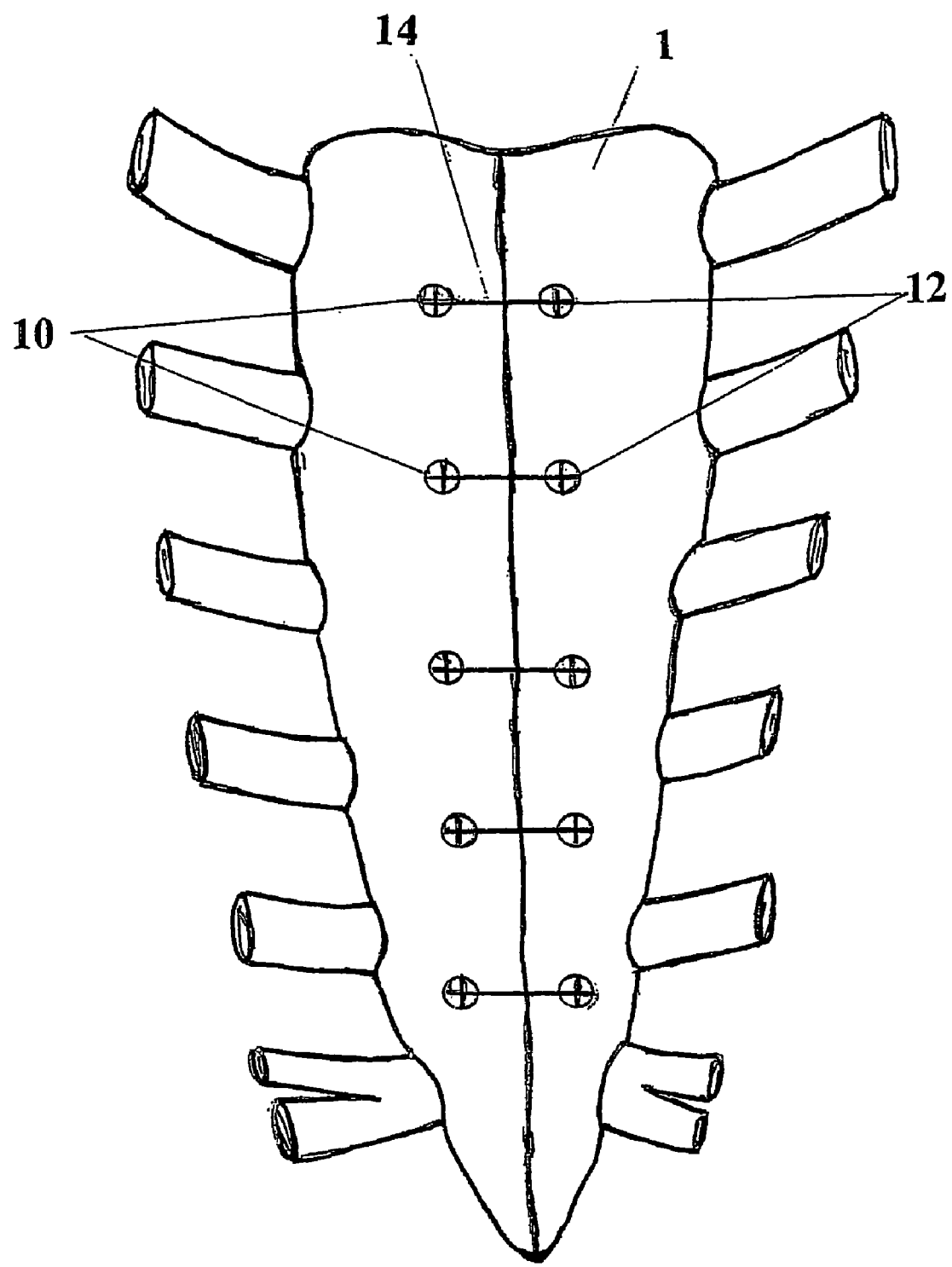
FIG. 3 is a diagram of reapproximating the sternum halves on completion of a surgical procedure using the proposed system.
Figure 4:
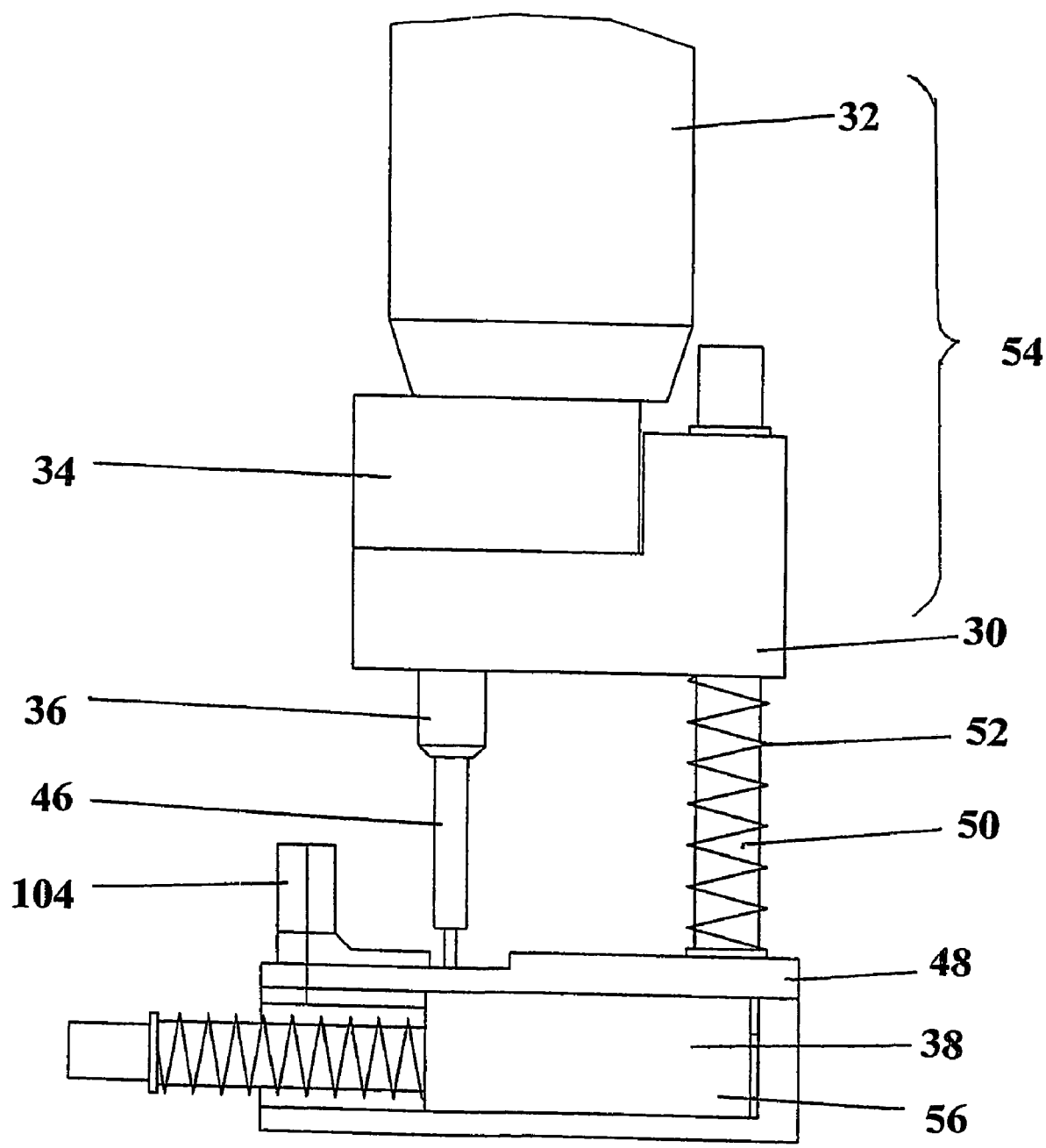
FIGS. 4-12 are views of the first embodiment of an apparatus for simultaneous placing of pairs of anchor means, more concrete.

Screws 10 and 12 may be set in pairs simultaneously in sternum 1 (FIG. 2) before incision of sternum 1, and on completion of the surgical procedure in thoracic cavity brought together and easily connected via fixing means—staple 14 (FIG. 3). Thereby there is provided a rigid and secure connection of screws 10 and 12 that may be released if necessary. Hence there is provided a rigid securing to one another of left half 3 and right half 5 of a patient's incised sternum 1 when carrying out a surgical procedure within thoracic cavity, and also separating left 3 right 5 halves of sternum 1 for post-operative emergency surgical procedures.

The screws 10 and 12 and the staples 14 made of FDA approved materials, mainly of metals and alloy group, consist of stainless steel, titanium, tantalum as well as titanium or tantalum alloys. The screws 10 and 12 and staples 14 also may be made of FDA approved biodegradable material.

The proposed system also comprises an apparatus 30 for simultaneous placing in sternum 1 both the first screw 10 adapted to be disposed within left half 3 of sternum 1, and second screw 12 adapted be disposed within right half 5 of sternum 1.

Each embodiment of the apparatus 30 for simultaneous placing of screws 10 and 12 (FIGS. 4, 5 and 13, 14) comprises a power means 32 for creating torque, means 34 for transmitting torque simultaneously to first 10 and second 12 screws, means 36 for searching and grasping simultaneously first and second screws 10 and 12, as well as means 38 for retaining and simultaneous delivering of these screws 10 and 12 to the aforesaid means 36 for their searching and grasping.

Power means 32 for creating torque (FIGS. 4, 5 and 13, 14) may be one of the means in a group including an electric, pneumatic or hydraulic motor. In the proposed embodiments power means 32 is an electric motor.

Figure 5:
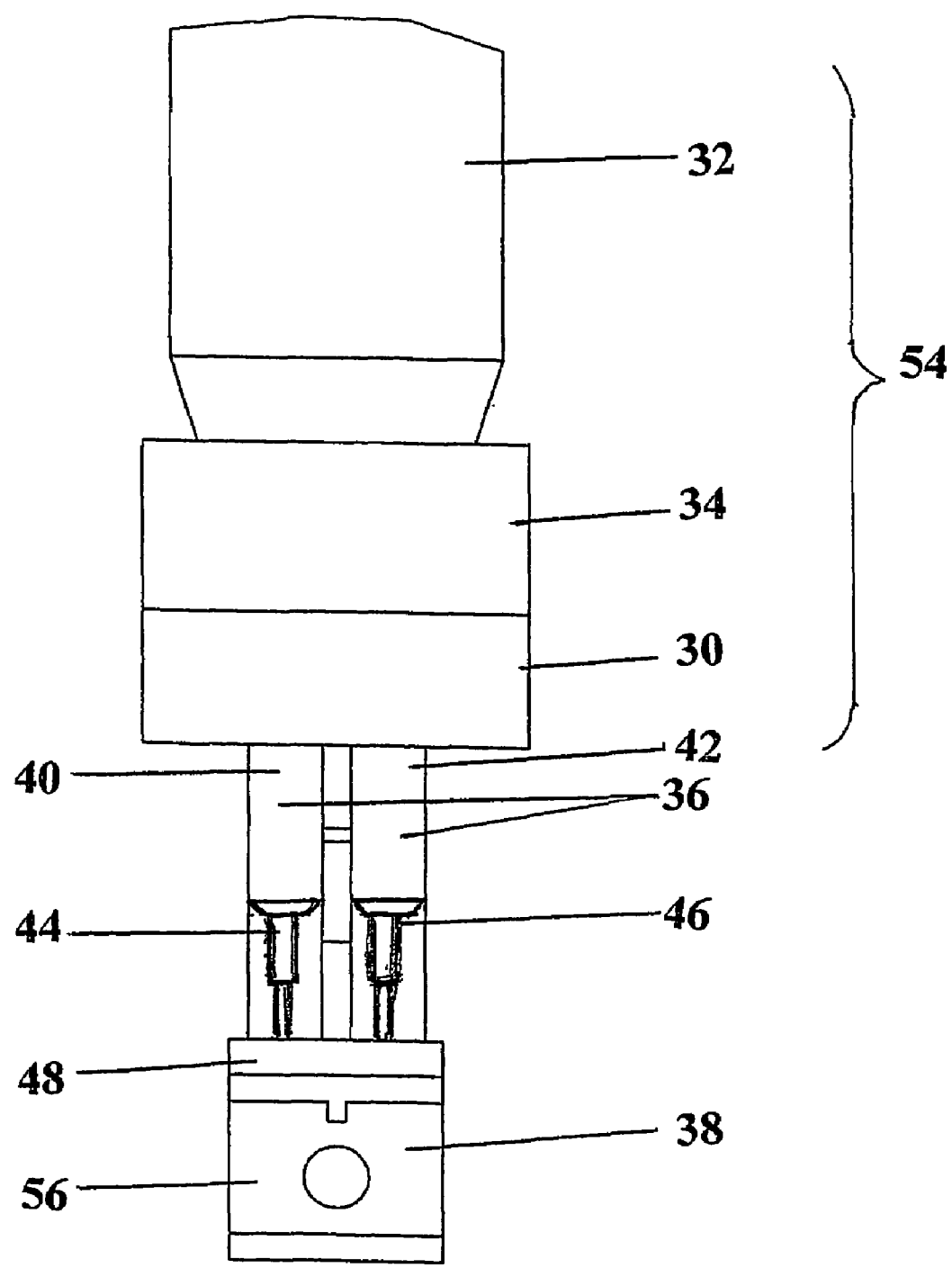
Figure 6:
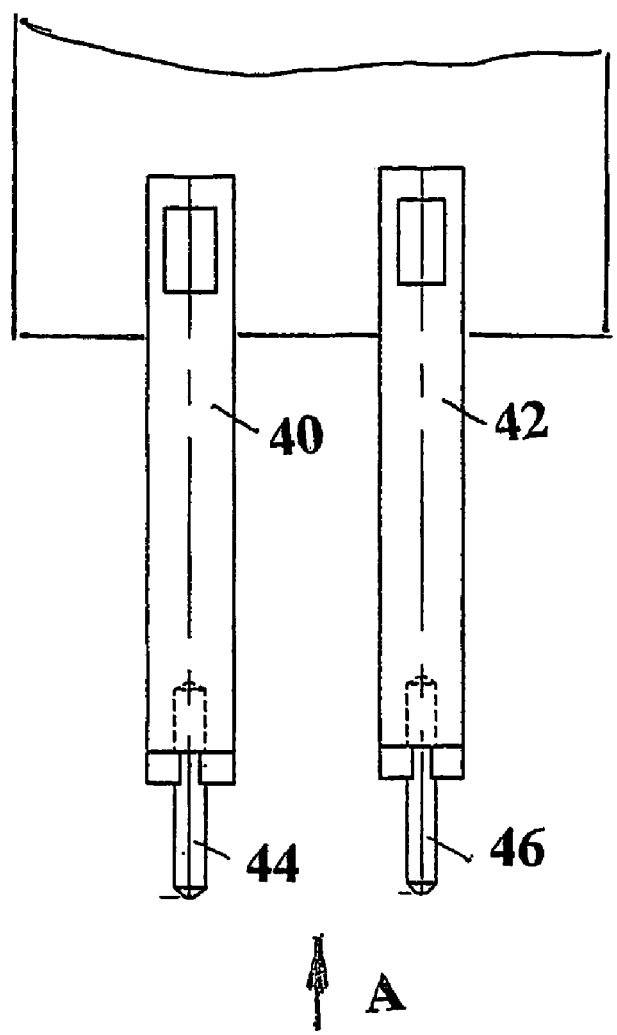
Figure 7:
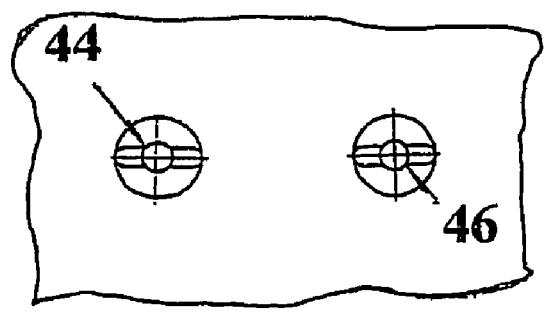
Figure 8:
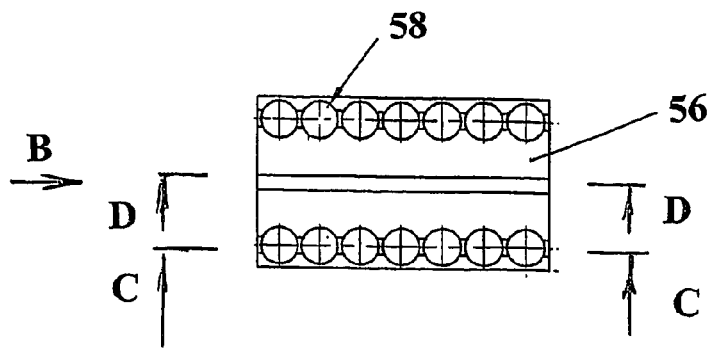
Figure 9:
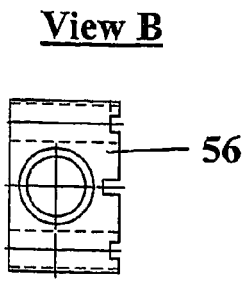
Figure 10:
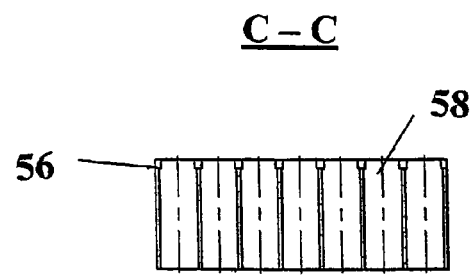
Figure 11:
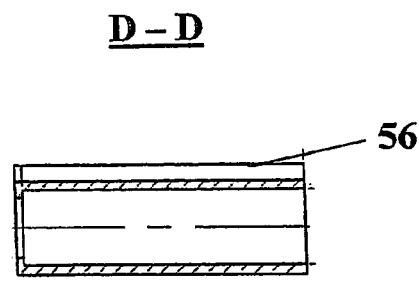

Means 34 for transmitting torque simultaneously to the first and second screws 10 and 12 (FIGS. 4, 5 and 13, 14) is a gear box 34 having one drive shaft 35 (see FIG. 14) and at least two driven shafts 40, 42. On driven shafts 40 and 42 of this gear box 34 there are mounted spring-loaded heads 44, 46, forming the means 36 for searching and grasping simultaneously first and second screws 10 and 12 (FIG. 5, 6, 7, 14).

The first embodiment of the apparatus 30 for simultaneously placing in the sternum first and second screws 10 and 12 (FIG. 4, 5) comprises a frame means—frame 48 with vertical guides 50 provided with springs 52. In described first embodiment of the apparatus 30 power means 32 for creating torque, means 34 for transmitting torque simultaneously to first and second screws 10 and 12, as well as means 36 for searching and grasping simultaneously first and second screws 10 and 12 are formed as a single unit 54, disposed on vertical guides 50 of frame 48 reciprocably relative to this frame 48.

In this first embodiment means 38 for retaining and simultaneously delivering first and second screws 10 and 12 to means 36 for their searching and grasping is a spring-loaded cartridge 56 disposed within this frame 48 adapted for stepping horizontal movement towards means 36 for searching and grasping. Cartridge means 56 comprises guides and two parallel rows of nests 58 for disposing screws 10 and 12 therein, and stops 104 (FIGS. 4, 5 and 8-11).

Figure 13:
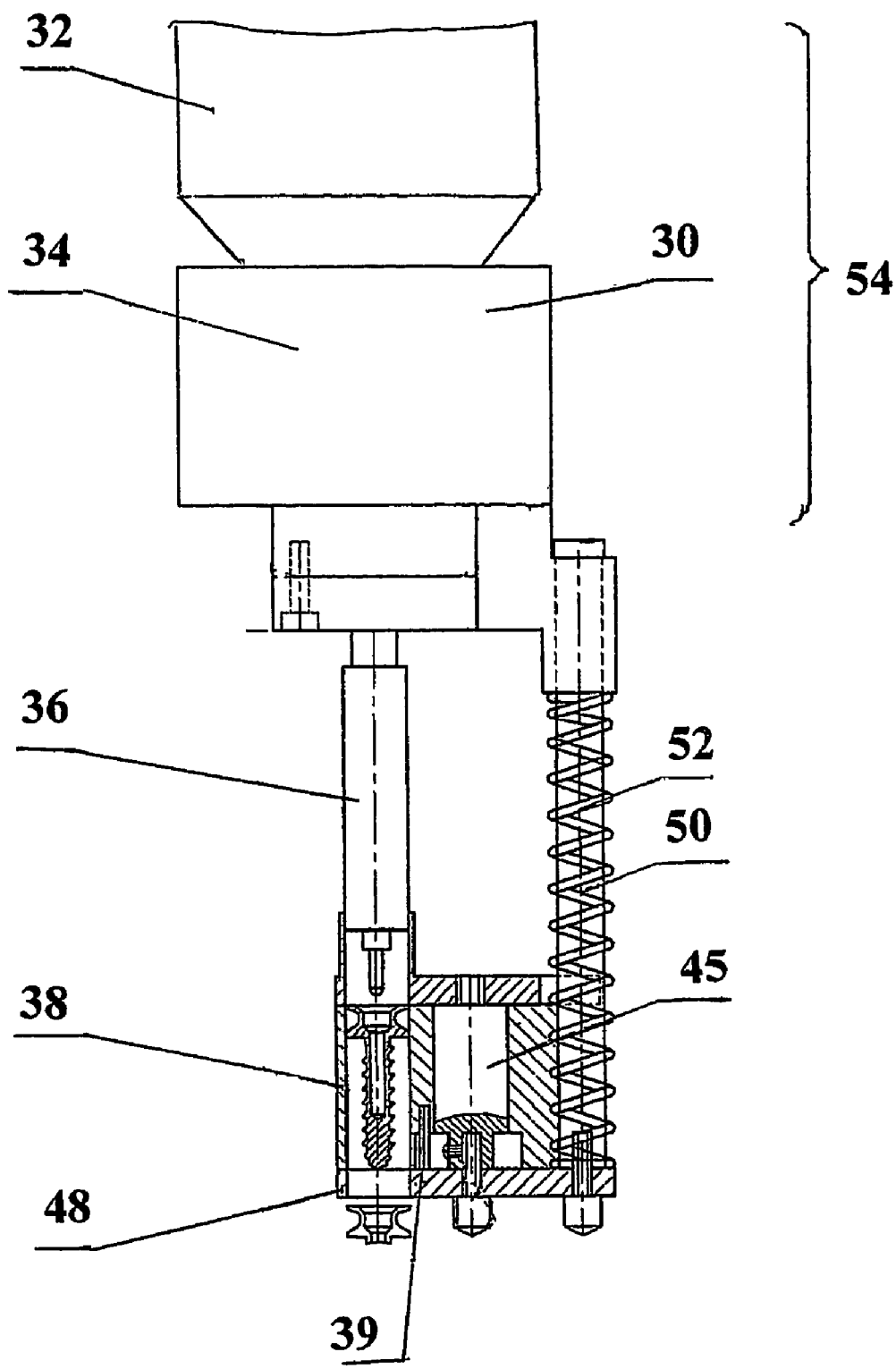
FIGS. 13-18 are views of the second embodiment of an apparatus for simultaneous placing of pairs of anchor means, more concrete.
Figure 14:
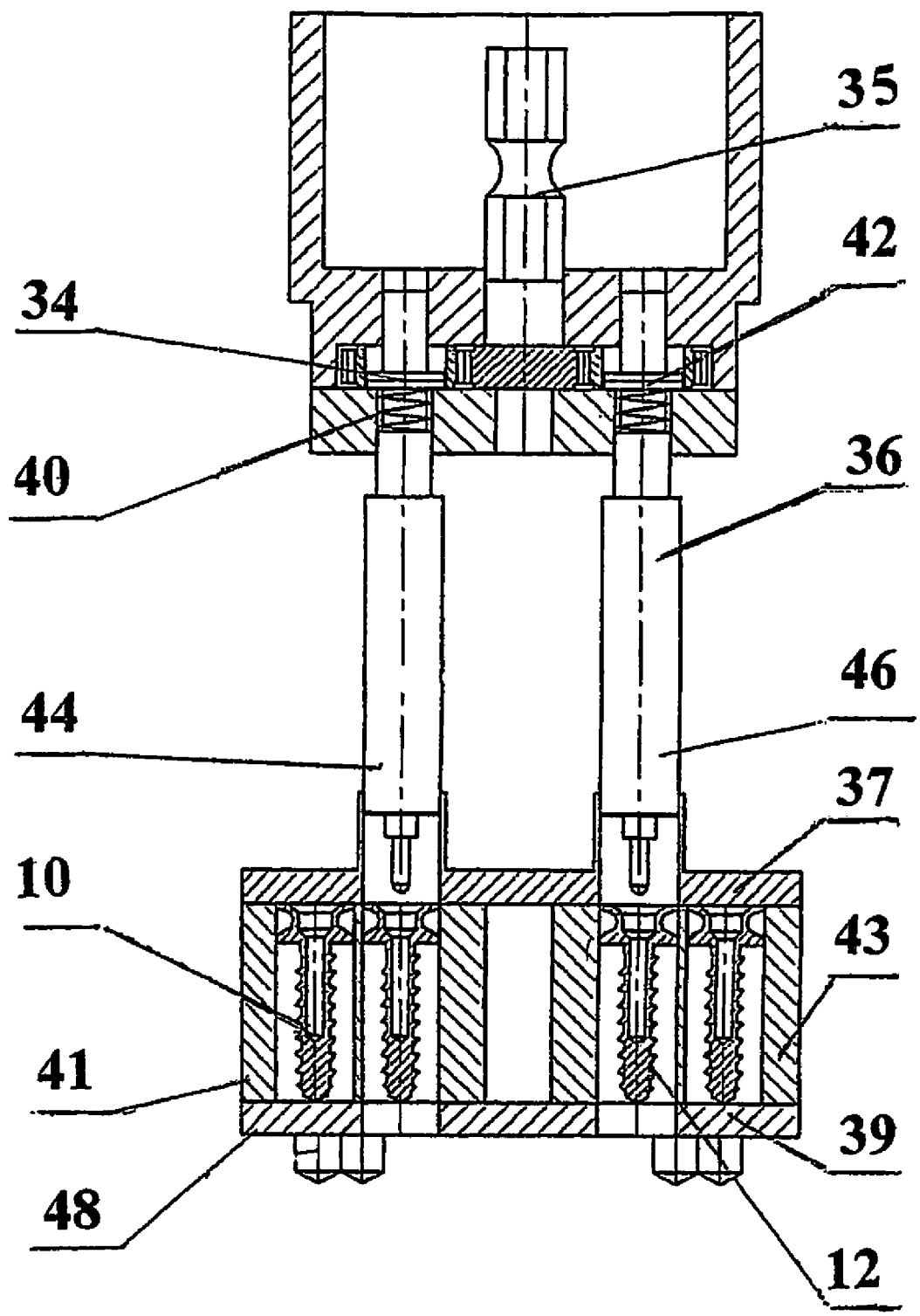

In the second embodiment apparatus 30 for simultaneously placing in the sternum the first and second anchor means (FIG. 13-14) contains a frame means—frame 48 with at least one vertical guide 50 provided with a spring 52 and two horizontal plates 37 and 39 disposed in parallel relationship. At least one vertical guide 50 is rigidly connected with at least one of these plates, in this case, plate 39. The means for retaining and simultaneously bringing the first and second anchor means to the means for their searching and grasping contains two spring-loaded rotary drums 41 and 43 disposed between plates 37 and 39 within frame means 48 to perform stepping synchronous swinging about their vertical axes 45 in direction to the means for searching and grasping 36 of these anchor means—screws 10 and 12 (FIG. 13-14).

In this embodiment, as in the previous one, power means 32 for generating torque, means for transmitting torque 34 simultaneously to the first and said second anchor means and means for searching 36 simultaneously the first and second anchor means are formed as a single unit 54 disposed at least on one vertical guide 50 of frame means 48 to reciprocate relative to the latter.

The proposed system also comprises a fixing apparatus for placing fixing means—staple 14 (FIGS. 19-24 and 25-27).

According to the first embodiment, the proposed fixing apparatus 60 for placing and removing fixing means—staple 14 comprises at least two levers, a first 62 and a second 64, each having a proximal end, 66 and 68, respectively, and a distal end, 70 and 72, respectively. These two levers, first 62 and second 64 are pivotally attached to one another via pin 74 and spring-loaded relative to one another via spring 76. Besides, the levers, first 62 and second 64 are provided with handles, respectively 78 and 80, at their distal ends 70 and 72, as well as with means for grasping heads of the screws 10 and 12 disposed at their proximal ends 66 and 68 (FIGS. 19, 20 and 21-24). The means for grasping heads of screws 10 and 12 comprise two protrusions 82 and 84 facing one another, one of them, 82 respectively, being disposed at the proximal end of first lever 62, and second, 84, at the proximal end of second lever 64, and these protrusions 82 and 84 have at their free ends recesses matching in shape grooves 22 on the side surface of heads of respective screws 10 and 12.

Fixing apparatus 60 also has at least one spring-loaded third lever 86 pivotally attached via pin 88 to second lever 64 and provided with a handle 90 at its distal end 92. At its proximal end 94 third lever 86 is provided with a means for delivering the fixing means—staples 14 simultaneously inside these first and second screws 10 and 12, which is substantially a pusher 96. Besides, fixing apparatus 60 has a means for retaining and by the piece delivering staples 14 comprising generally a movable spring-loaded die 98 with grooves 100 for disposing staples 14 (FIGS. 19, 20 and 21-24).

Die 98 with grooves 100 for disposing staples 14 is mounted to perform stepping linear movement, in a guide 102. This guide 102 is rigidly attached to first lever 62 or to second lever 64 of fixing apparatus 60 and provided of stops 110.

Figure 25:
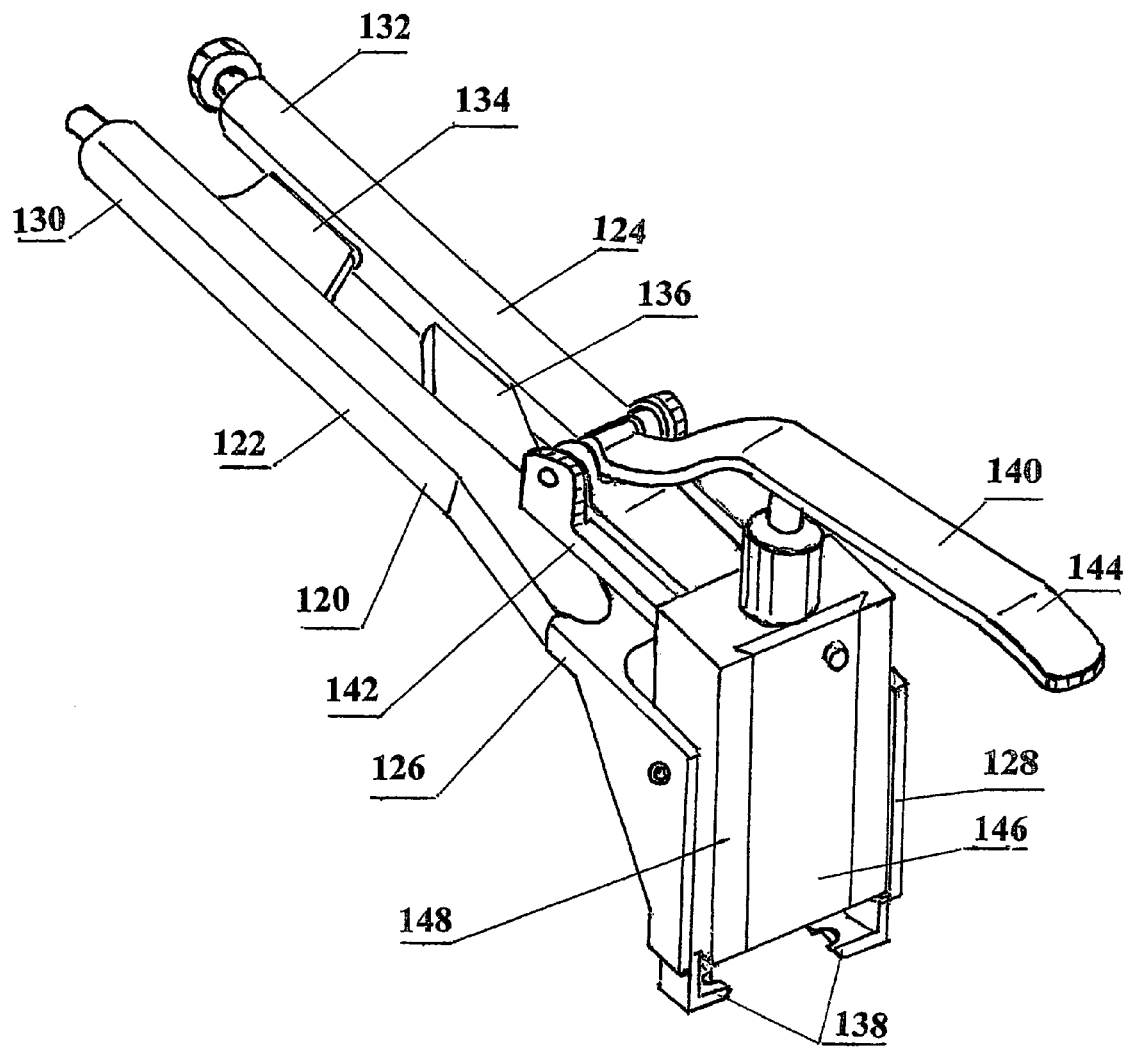
FIG. 25, 26 are the general views of the second embodiment of the fixing apparatus.
Figure 26:
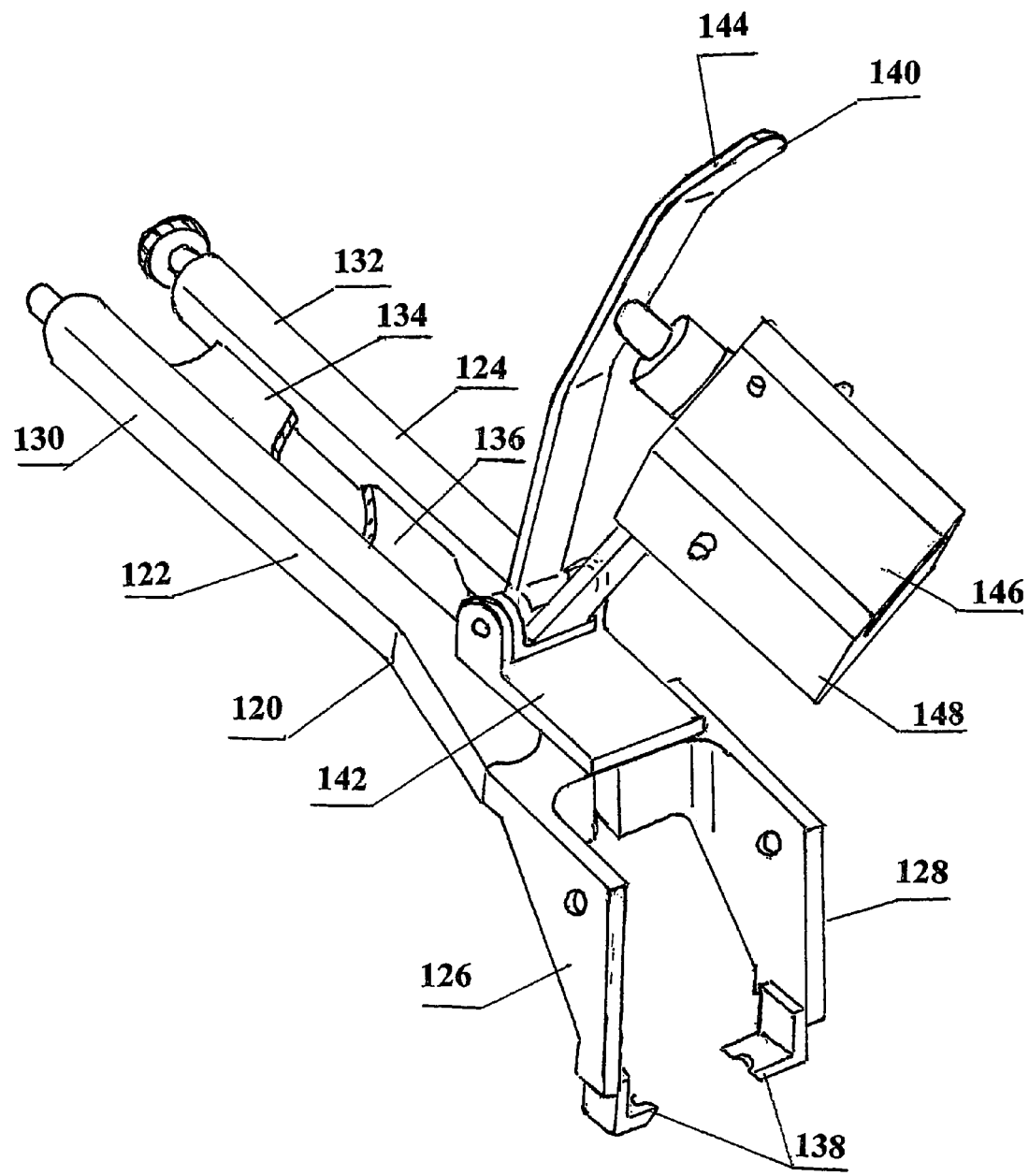

According to the second embodiment fixing apparatus 120 for placing the fixing means—staple 14 (FIG. 25, 26) contains at least two levers, first 122 and second 124, each of them having a proximal end and distal end, respectively 126, 128 and 130, 132. These levers 122 and 124 are connected with one another and provided with handles at their distal ends, with means for mutual fixing of handles when brought together—stops 134, 136 as well as means for grasping the heads of anchor means—grips 138 at their proximal ends 126 and 128. Apparatus 120 also contains at least one third lever 140 pivotally connected with bearing plate 142 rigidly mounted on the first lever 122 or second lever 124 (FIG. 25, 26). This third lever 140 is provided with handle 144 at its free end, and by its middle pivotally connected with a means for delivering the fixing means inside the first and second anchor means formed substantially as a pusher 146. Besides, apparatus 120 contains a means for retaining and by the piece delivery of fixing means formed substantially as a cartridge 148, wherein there are disposed right up to one another fixing means—staples 14.

In this embodiment apparatus 120 also has means for grasping the heads of anchor means—grips 138 which are formed as two protrusions facing one another one of which is located at the proximal end 126 of first lever 122, and the second at the proximal end 128 of second lever 124 (FIG. 25, 26). These protrusions have at their free ends recesses matching in shape the grooves 22 on the side surface of the heads of anchor means—screws 10 and 12.

In the second embodiment, fixing apparatus 120 contains at least one third lever 140, means for retaining and by the piece delivery of fixing means formed substantially as a cartridge 148, as well as a means for delivering the first and second anchor means formed substantially as a pusher 146, all these forming a single unit. The single unit is pivotally connected with bearing plate 142 rigidly secured on first lever 122 or second lever 124 and is capable of folding back in the vertical plane to provide viewing the means for grasping anchor means—screws 10, 12 or returning into operative position with simultaneous rigid fixing of cartridge 148 at proximal ends 126, 128 of first and second levers 122, 124 of fixing apparatus 120 (FIG. 25, 26).

Figure 27:
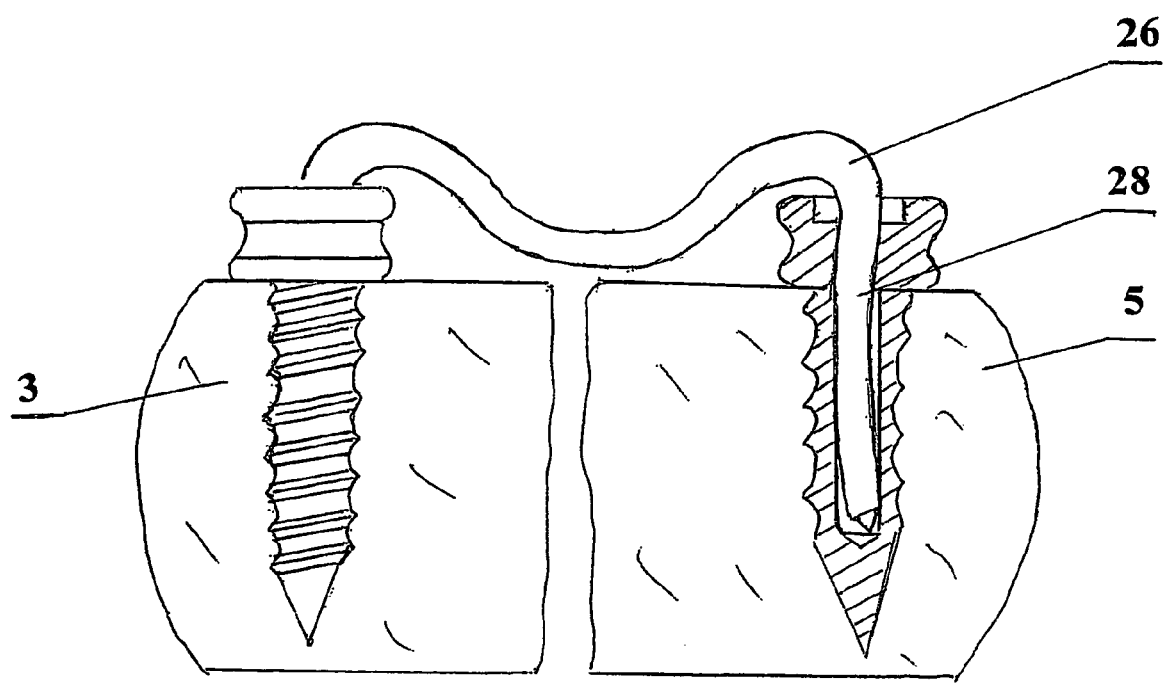
FIG. 27 is a second embodiment of the fixing means.

FIG. 27 shows staple body 26 curved in such a way that its middle approximates the surface of the left 3 and right 5 halves of sternum, two legs 28 of fixing means 14 being slightly curved.

Figure 28:
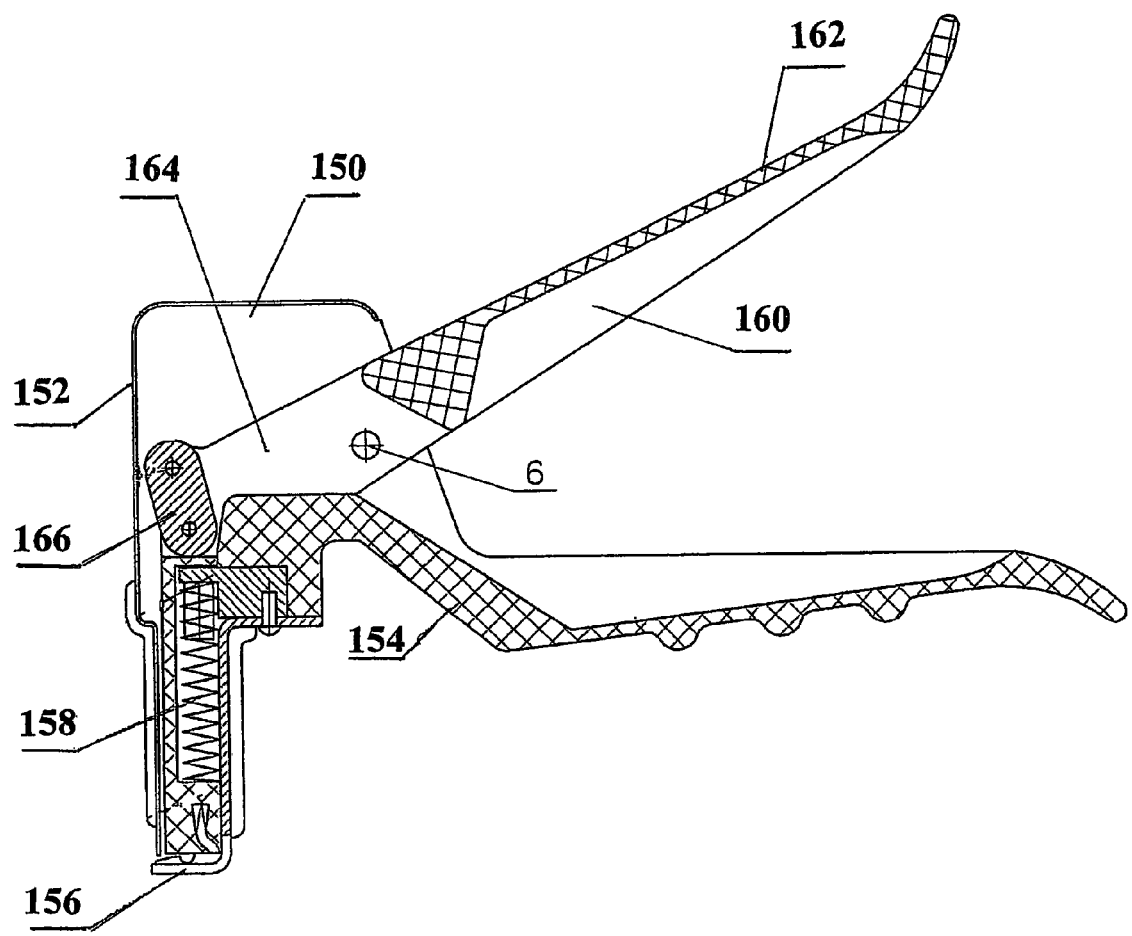
FIG. 28 is the longitudinal section of the proposed apparatus for removing the fixing means.
Figure 29:
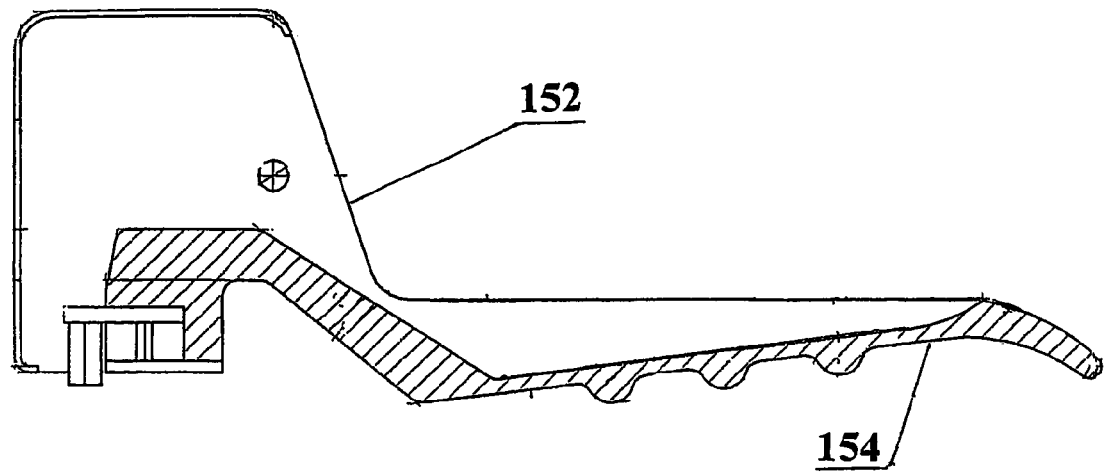
FIG. 29, 30 are longitudinal sections of the body and pressure lever of the proposed apparatus for removing the fixing means.
Figure 30:
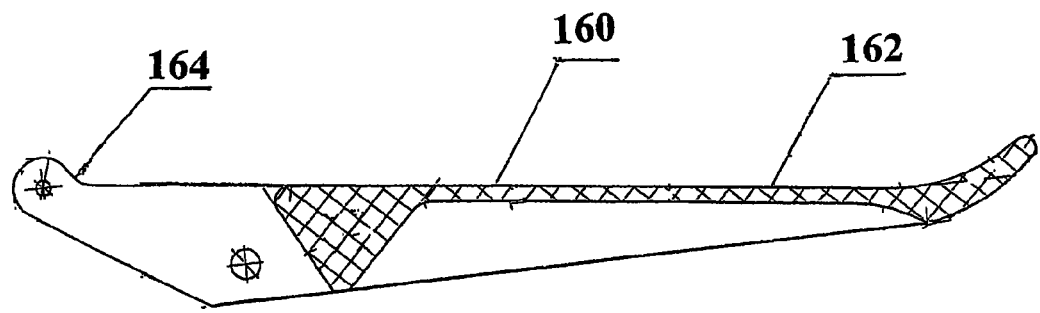
Figure 31:
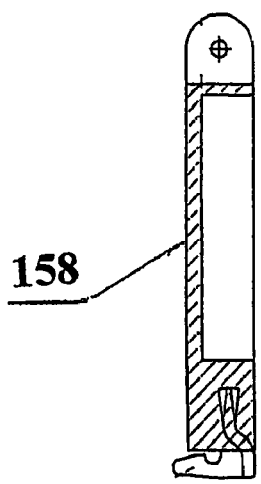
FIG. 31-35 are the views of a spring-loaded grasping means and stop of the proposed apparatus for removing the fixing means.
Figure 32:
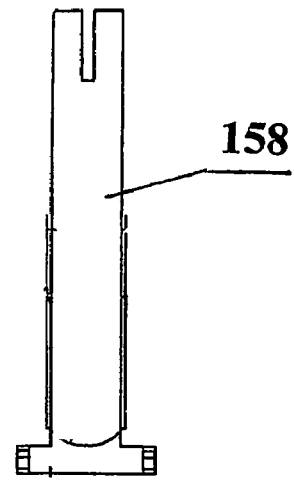
Figure 33:
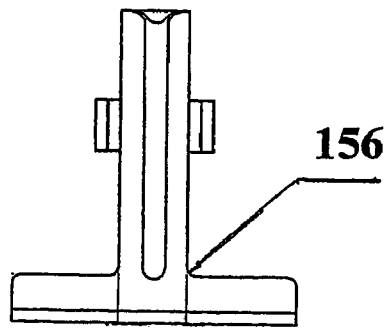
Figure 34:
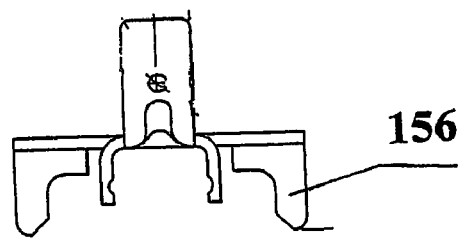
Figure 35:
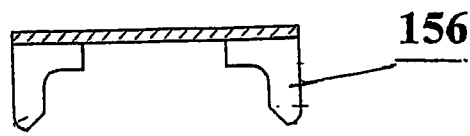

And at last, the system comprises an apparatus 150 for removing the fixing means when it is necessary to perform a post-operative surgical procedure within the thoracic cavity (FIG. 28). In contains a hollow body 152 provided with a handle 154 extending therefrom, and in its lower part—with a bifurcated stop 156. There is also a spring-loaded grasping member 158 movably located within this body 152 and a pressure lever 160 pivotally secured within the upper part of this hollow body 152. This pressure lever 160 has a handle 162 extending substantially in the same direction as handle 154 of hollow body 152, and a free end 164 disposed within hollow body 152 and operatively connected with the spring-loaded grasping member 158 via shackle 166. The apparatus is shown in more detail in FIG. 28-35.

The system disclosed in the present invention operates according to the claimed sternal closure method by re-approximating left half 3 and right half 5 of patient's sternum 1 during a surgical procedure within the thoracic cavity. This method includes several successive steps.

First, before incising sternum 1 into left 3 and right 5 halves, penetrating of several pairs of anchor means—screws 10 and 12 is performed. This work is carried out by apparatus 30 so that one of these screws 10 is placed in future left half 3 of the sternum, and the second—12 in future right half 5 of the sternum 1. Screws 10 are adapted to be disposed within left half 3 of sternum 1, and other screws 12 are adapted to be disposed within right half 5 of sternum 1. To this end, apparatus 30 is placed onto the surface of sternum 1.

Then unit 54 is lowered along guides 50 overcoming the resistance of springs 52, until spring-loaded heads 44, 46 forming means 36 for searching and grasping simultaneously first and second screws 10 and 12 (FIG. 4, 5, 6, 7) grasp their heads 18 and 20. Continuing to move unit 54 downwards, screws 10 and 12 are rotated and simultaneously extended from cartridge means 56 or drums 41, 43, forcing them to screw into sternum 1. Next, unit 54 is released and, under the action of springs 52, returns to the initial position. Therewith spring-loaded cartridge means 56 or drums 41, 43 released from the first pair of screws 10 and 12, automatically move to readiness position when heads of the following pair of screws 10 and 12 come in contact with stops. Apparatus 30 is again ready for operation.

The procedure of placing pairs of screws 10 and 12 is repeated as many times as necessary to provide, on completion of a surgical procedure, secure connection of left 3 and right 5 halves of sternum 1.

Then apparatus 30 is removed and sternum 1 is incised, by a surgical procedure and using common surgical means, into left 3 and right 5 halves. Thereupon the surgical operation is performed. On completion of the surgical operation within thoracic cavity, left 3 and right 5 halves of sternum 1 are re-approximated using conventional techniques.

Next, fixing apparatus 60 is applied, performing the grasping, via protrusions 82 and 84 of its levers 62 and 64, of first and second screws 10 and 12 by their heads 18 and 20. Bringing together levers 62 and 64, left 3 and right 5 halves of incised sternum 1 are re-approximated at a necessary distance. Guide 102 for die 98 serves as a stop defining the terminal position of levers 62 and 64.

Then, by pressing handle 90 of lever 86, pusher 96 is moved downwards, and thus staple 14 extended from groove 100 of die 102, placed and tightly fixed in passages 29 of screws 10 and 12. Staple 14 rigidly connects heads of first 10 and second 12 screws. Hence, there is formed a rigid connection of left 3 and right 5 halves of incised sternum 1. Further, spring-loaded handle 90 of lever 86 is released to extend pusher 96 from spring-loaded die 102. Die 102 automatically moves to the next position, where next staple 14 disposed in groove 100 comes in contact with stop 104. Fixing apparatus 60 is again ready for operation.

The final operation of placing staple 14 is repeated as many times as there are corresponding pairs of screws 10 and 12.

Using the fixing apparatus 120, first and second screws 10 and 12 are grasped by their heads 18 and 20 via protrusions of levers 122 and 124 of this apparatus. Approximating levers 122 and 124 the left 3 and right 5 halves of separated sternum 1 are brought together at a necessary distance. In this case levers 122 and 124 are rigidly fixed together via locks 134, 136 (FIG. 25, 26).

In the process of bringing together levers 122 and 124 the single unit including at least one third lever 140, means for retaining and by the piece delivery of fixing means formed substantially as a cartridge 148, as well as a means for delivering the fixing means within the first and second anchor means which is formed substantially as a pusher 146 (FIG. 25, 26), folds back in the vertical plane to provide viewing grips 138 for anchor means-screws 10, 12. After rigid mutual fixing of levers 122 and 124, the single unit is returned into operative position simultaneously fixing the cartridge 148 at proximal ends 126, 128 of first and second levers 122, 124 of fixing apparatus 120.

Then, by pressing the handle 144 of third lever 140, pusher 146 is moved downwards and thus staple 14 is withdrawn from cartridge 148, placed and fixed tightly in ducts 29 of screws 10 and 12. Staple 14 rigidly connects the heads of first 10 and second 12 screws. Thereby there is created a rigid connection of left 3 and right 5 halves of separated sternum 1.

Afterwards, releasing handle 144 of lever 140, pusher 146 is withdrawn from cartridge 148. Therewith, next staple 14 located in cartridge 148 automatically moves to readiness position. Fixing apparatus 120 is again ready for operation. The final step in placing staple 14 is repeated as many times as there are respective pairs of screws 10 and 12.

When it is necessary to perform a post-operative surgical procedure within the thoracic cavity, the rigid connection of screws 10 and 12 with staple 14 may be disassembled via apparatus 150 for removing the fixing means. To this effect staple 14 is hooked by spring-loaded grasping member 158 of apparatus 150 movably disposed within body 152, and the pressure lever 160 pivotally mounted within the upper part of hollow body 152 is turned. This pressure lever 160 operatively connected with spring-loaded grasping member 158 moves the latter relative to the stops of apparatus 150 and hence withdraw staple 14 from screws 10 and 12. This procedure is repeated as many times as many staples have to be withdrawn. Then there is performed a post-operative surgical procedure within the thoracic cavity. Further, if necessary, the procedure of assembling a rigid connection of screws 10 and 12 with staples 14 may be repeated again.

The application of the claimed system of means, method and apparatus permits to perform fast securing to one another of left half 3 and right half 5 of incised patient's sternum 1 during a surgical procedure within thoracic cavity, as well as severing left 3 and right 5 halves of sternum 1 in case of urgent operations.

Thus there is provided secure connection of a patient's sternum by arranging the fixing means evenly along the sternum incision line irrespective of its configuration. Besides, there is provided easy placing and, if necessary, removing these fixing means, as well as efficacy and convenience in a surgeons work.

The durable and reliable fixation of the sternum is provided by manufacturing of the anchor means and staples from FDA approved materials, mainly of metals and alloy group, consist of stainless steel, titanium, tantalum as well as the titanium or tantalum alloys. The anchor means and staples also may be made of FDA approved biodegradable material, thus allowing dissolvation of all fixation means between 8-10 months after full repair of the sternal halves, shortening of the perioperative time and reducing patient's moral trauma.

It should be understood that while the above is a complete description of the preferred embodiments of the invention, various alternatives, modifications and equivalents may be used. Therefore, the above description should not be taken as limiting the scope of the invention which is defined by the following claims.

The invention claimed is:

1. A sternal closure system for maintaining left and right halves of a patient's longitudinally incised sternum in proper spaced relationship during a surgical procedure in the thoracic cavity, the system comprising:
a first anchor having an inner axial passage, configured to be disposed within the left half of the sternum;
a second anchor having an inner axial passage, configured to be disposed within the right half of the sternum; and
a rigid fastener made of a metallic material and defined by a body portion having two legs each being configured for repeated insertion into and withdrawal from a respective one of said inner axial passages when the first anchor and the second anchor are disposed within respective halves of the sternum, the body portion of the rigid fastener configured to externally extend across an incision of the incised sternum between the first anchor and second anchor while said legs are removably tightly held within the inner axial passages, the rigid fastener configured to maintain the left half of the sternum and the right half of the sternum in relative position upon reapproximation; and
a fixing apparatus for simultaneous linear displacement of the first and second anchor so as to bring the first and second anchor closer together and thus to reapproximate the left half of the sternum and the right half of the incised sternum, said fixing apparatus being capable to secure the first and second anchor in their relative position upon reapproximation of the left and right half of the incised sternum and said fixed apparatus is to removably insert the legs of said rigid fixing into respective longitudinal passages of said first and second anchor upon bringing the first and second anchor means closer together.

2. A sternal closure system as defined in claim 1, further comprising an apparatus for removing legs of said rigid fixing from respective longitudinal passages of said first and second anchor and separating the rigid fixing from the first and second anchor when necessary.

3. A sternal closure system configured for reapproximating left and right halves of a patient's longitudinally incised sternum during a surgical procedure in the thoracic cavity, the system comprising:
a first, at least one anchor having an inner axial passage, configured to be disposed inside the left half of the sternum;
a second, at least one anchor having an inner axial passage, configured to be disposed inside the right half of the sternum; and
at least one rigid fixing element made of a metallic material, said fixing element comprising a staple defined by a body portion and by two legs extending orthogonally from the body portion, said legs being configured for insertion in respective axial passages of said first and second anchors so as upon insertion, to rigidly connect said first, at least one anchor, disposed within the left half of the sternum, to said second, at least one anchor disposed within the right half of the sternum, the body portion of the rigid fixing element configured to externally extend across an incision of the incised sternum between first and second anchors with said legs of the rigid fixing element being removably tightly held within the respective axial passages of the first and second anchors, the rigid fixing element configured to maintain the left half of the sternum and the right half of the sternum in relative position for reapproximation, and
a fixing apparatus configured for simultaneous linear displacement of the first and second anchors in a direction across the incision of the incised sternum so as to bring the first and second anchors closer together and thus to reapproximate the left half of the incised sternum and the right half of the incised sternum, said fixing apparatus configured to be capable of securing the first and second anchors in their relative positions upon reapproximation of the left and right halves of the incised sternum and said fixing apparatus is configured to removably insert the legs of said rigid fixing element into respective longitudinal passages of said first and second anchors upon bringing the first and second anchors together,
the legs of said rigid fixing element being configured for subsequent extraction from the respective axial passages so as to facilitate separation of the left and right halves of the sternum when necessary, and for re-insertion of the fixing element therein.

4. A system according to claim 3, wherein said first, at least one anchor, configured to be disposed within the left half of the sternum, and said second, at least one anchor, configured to be disposed within the right half of the sternum, are screws having an external thread of one direction.

5. A system according to claim 3, wherein said first, at least one anchor, configured to be disposed within the left half of the sternum, and said second, at least one anchor, configured to be disposed within the right half of the sternum, are screws having an external thread of different directions.

6. A system according to claim 3, wherein said first, at least one anchor, configured to be disposed within the left half of the sternum, and said second, at least one anchor, configured to be disposed within the right half of the sternum, have heads provided with elements for grasping and rotating them by said apparatus for simultaneous placing of said anchors.

7. A system according to claim 6, wherein the heads of said first and said second anchors are provided with elements for their grasping by said apparatus for simultaneously placing said anchors, said grasping elements being generally shaped as grooves on the side surface of said heads.

8. A system according to claim 6, wherein the heads of said first and said second anchors are provided with elements for their rotation by said apparatus for simultaneously placing said anchors, and the elements for their rotation are generally cross-shaped slots on the end surface of said heads.

9. A system according to claim 6, wherein the heads of said first and said second anchors are provided with elements for their rotation by said apparatus for simultaneous placing of said anchors, and the elements for rotation are substantially shaped as hexahedral holes in the end face of said heads.

10. A system according to claim 3, wherein said at least one fixing element is substantially shaped as a staple having a body and at least two legs extending from the body in a substantially perpendicular relationship, whereby said staple is configured for rigidly connecting said first, at least one anchor, to said second, at least one anchor.

11. A system according to claim 10, wherein said at least one fixing element is formed as a staple having a curved body and at least two slightly curved legs for tightly disposing in a respective inner axial passage of said first, at least one anchor configured to be disposed in the left half of the sternum, and said second, at least one anchor configured to be disposed in the right half of the sternum.

12. A system according to claim 3, wherein said first, at least one anchor, configured to be disposed within the left half of the sternum, said second, at least one anchor, configured to be disposed within the right half of the sternum, and said at least one fixing, are all made of FDA approved metal or alloy, mainly of one of metal or alloy of the group, consisting of stainless steel, titanium, tantalum, alloys of titanium and tantalum.

13. A system according to claim 3, wherein said first, at least one anchor, configured to be disposed within the left half of the sternum, said second, at least one anchor, configured to be disposed within the right half of the sternum, and said at least one fixing, are all comprised of FDA approved biodegradable material.

14. A system according to claim 3, further comprising an apparatus for simultaneously placing in the sternum first, at least one anchor, configured to be disposed within the left half of the sternum and said second, at least one anchor configured to be disposed within the right half of the sternum, said apparatus comprising:
   a power element to generate a torque;
   an element for transmitting torque simultaneously to said first and said second anchors;
   an element for searching and grasping simultaneously said first and said second anchors; and
   an element for retaining and simultaneously delivering said first and said second anchors to said element for their searching and grasping.

15. A system according to claim 14, wherein said power element for generating a torque comprises one of the members of a group consisting of an electric, pneumatic and hydraulic engine.

16. A system according to claim 14, wherein said element for transmitting torque simultaneously to said first and said second anchors comprises a gear box having one drive shaft and at least two driven shafts.

17. A system according to claim 16, wherein on the driven shafts of said gear box there are mounted spring-loaded heads forming said element for searching and grasping simultaneously said first and said second anchors.

18. A system according to claim 14, wherein said apparatus for simultaneously placing in the sternum said first, at least one anchor, configured to be disposed within the left half of the sternum, and said second, at least one anchor, configured to be disposed within the right half of the sternum, comprises a frame element with vertical guides, and said element for retaining and simultaneously delivering said first and said second anchors to said element for their searching and grasping comprises a spring-loaded cartridge disposed within said frame element.

19. A system according to claim 18 wherein, said element for retaining and simultaneously delivering said first and said second anchors to said element for their searching and grasping comprises a spring-loaded cartridge, disposed within said frame element and capable of stepping horizontal movement towards said element for searching and grasping said anchors.

20. A system according to claim 14, wherein said apparatus for simultaneously placing in the sternum said first, at least one anchor configured to be disposed within the left half of the sternum, and said second, at least one anchor configured to be disposed within the right half of the sternum, contains a frame element with two horizontal plates disposed in a parallel relationship to each other and at least one vertical guide rigidly connected to at least one of these plates, and said element for retaining and simultaneously delivering said first and said second anchors to said element for their searching and grasping contains two spring-loaded rotary drums disposed between the plates within said frame element.

21. A system according to claim 20, wherein said element for retaining and simultaneously delivering said first and said second anchors to said element for their searching and grasping contains two spring-loaded rotary drums disposed between the plates within said frame element configured to perform stepping synchronous swinging about their vertical axes towards said element for searching and grasping said anchors.

22. A system according to claim 14, wherein, in said apparatus for simultaneously placing in the sternum said first, at least one anchor, configured to be disposed within the left half of sternum, and said second, at least one anchor, configured to be disposed within the right half of sternum, said power element generating torque, transmitting torque simultaneously to said first and said second anchors, and element for searching and grasping simultaneously said first and said second anchor, are formed as a single unit disposed on said at least one vertical guide of said frame element reciprocably relative to the latter.

23. A system according to claim 3, in which the fixing apparatus comprises:
- at least first and second levers each having a proximal end and distal end, the levers being pivotally connected to one another and provided with handles at their distal ends and with element for grasping heads of anchors at their proximal ends, the arrangement being such that upon relative pivoting of either the first or the second lever, said grasping heads are simultaneously linearly displaceable and can be brought closer together;
- at least one third lever pivotally connected to said first lever or said second lever and provided with a handle at its distal end, and at its proximal end with an element for delivering the legs of the rigid fixing element inside respective longitudinal passages of said first and said second anchors, said third lever being formed substantially as a pusher;
- an element for retaining and by the piece delivering of rigid fixing elements, formed substantially as a movable spring-loaded die with slots for disposing rigid fixing elements.

24. A system according to claim 23, wherein said fixing apparatus further comprises at least first and second levers each having a proximal end and a distal end, the first and second levers being pivotally connected to each other, spring-loaded relative to each another and provided with handles at their distal ends, and an element for grasping the heads of anchors at their proximal ends.

25. A system according to claim 23, wherein said elements for grasping the heads of anchors are formed as two protrusions facing one another, one of them being disposed at the proximal end of first lever, and the second at the proximal end of second lever, and these protrusions have, at their free ends, recesses matching a shape of grooves on side surfaces of heads of said anchors.

26. A system according to claim 23, wherein said fixing apparatus further comprises at least one third lever pivotally connected to said first lever or said second lever and spring-loaded relative to the first or second levers, said third lever being provided with a handle at its distal end, and at its proximal end with an element for delivering the fixing inside said first and said second anchors, which is shaped substantially as a pusher.

27. A system according to claim 23, wherein said fixing apparatus has an element for retaining and by the piece delivering of fixing elements, comprising generally a movable spring-loaded die with slots for disposing the fixing element, the die being configured to perform stepping linear movement in a guide, which is rigidly connected to said first lever or to said second lever of said fixing apparatus.

28. A system according to claim 3, further comprising a fixing apparatus for placing said fixing elements, the fixing apparatus comprising:
- at least two levers, the first and the second, each of them having a proximal end and a distal end, the at least two levers being pivotally connected to one another and provided with handles at their distal ends, as well as with an element for grasping heads of anchors at their proximal ends;
- at least one third lever pivotally connected to a bearing plate rigidly secured on said first lever or said second lever, the third lever having a handle at its free end, and pivotally connected by its middle to the element for delivering the fixing elements inside first and said second anchors formed substantially as a pusher;
- an element for retaining and by the piece delivering of fixing elements formed substantially as a cartridge enclosing spring-loaded fixing element located right up to one another.

29. A system according to claim 28, wherein said fixing apparatus contains at least two levers, the first and the second, each of them having a proximal end and a distal end, these levers are pivotally connected to one another and provided with handles at their distal ends, an element for mutually fixing the handles when brought together, as well as by elements for grasping the heads of anchors at their proximal ends.

30. A system according to claim 29, wherein said elements for grasping the heads of anchors are configured as two protrusions facing one another, one of which is disposed at the proximal end of the first lever, and the second at the proximal end of the second lever, and the protrusions having at their free ends recesses matching a shape of grooves on side surfaces of the heads of said anchors.

31. A system according to claim 28, wherein said fixing apparatus contains a single unit including at least one third lever, an element for retaining and by the piece delivery of fixing elements formed substantially as a cartridge, and an element for delivering a fixing element inside said first and said second anchors formed substantially as a pusher, this single unit is pivotally connected to the bearing plate rigidly mounted on said first lever or said second lever and is capable of folding back in the vertical plane to provide viewing of said element for grasping the anchors or returning into operative position with simultaneous rigid fixing of the cartridge at the proximal ends of said first and second levers of the fixing apparatus.

32. A system according to claim 3, further comprising an apparatus for removing said fixing elements when it is necessary to perform a post-operative surgical procedure within the thoracic cavity, the apparatus for removing comprising:
- a hollow body provided with a handle extending therefrom, and in its lower part, a bifurcated stop;
- a spring-loaded grasping member movably disposed within the hollow body; and
- a pressure lever pivotally mounted on a pin within the upper part of the hollow body, the pressure lever having a handle extending substantially in the same direction as said handle of the hollow body and a free end located within the hollow body and operatively connected to said spring-loaded grasping member.

33. A system according to claim 3, further comprising an apparatus for simultaneously placing in the sternum said first, at least one anchor, configured for disposing within the left half of the sternum, and said second, at least one anchor, configured to be disposed within the right half of the sternum.

34. A system according to claim 3, further comprising a fixing apparatus for placing said fixing elements configured for rigidly and releasably connecting said first, at least one anchor, configured to be disposed within the left half of the sternum and said second, at least one anchor, configured to be disposed within the right half of the sternum, whereby there is performed a rigid connection to one another of the left and the right halves of the sternum during a surgical procedure within the thoracic cavity.

35. A system according to claim 3, further comprising an apparatus for removing said fixing elements when it is necessary to perform a post-operative surgical procedure in the thoracic cavity, facilitating separation of the left and right halves of sternum closed in this way, in case of post-operative emergency surgical procedures.

* * * * *